United States Patent [19]
Hawkins et al.

[11] Patent Number: 5,663,059
[45] Date of Patent: Sep. 2, 1997

[54] HUMAN PHOSPHOLIPASE INHIBITOR

[75] Inventors: Phillip R. Hawkins, Mountain View; Lynn E. Murry, Portola Valley, both of Calif.

[73] Assignee: Incyte Pharmaceuticals, Inc., Palo Alto, Calif.

[21] Appl. No.: 652,859

[22] Filed: May 23, 1996

Related U.S. Application Data

[63] Continuation-in-part of Ser. No. 644,754, May 10, 1996.

[51] Int. Cl.$^6$ .............. C12N 15/00; C12N 15/12; C12N 15/63; C12N 15/85
[52] U.S. Cl. .............. 435/69.2; 435/325; 435/320.1; 435/348; 435/419; 536/23.5
[58] Field of Search ............ 536/23.5; 435/320.1, 435/240.2, 69.2

[56] References Cited

PUBLICATIONS

Ohkura N, et al. "The two subunits of a phospholipase A2 inhibitor from the plasma of thailand cobra having structural similarity to urokinase-type plasminogen activator receptor and ly-6 related proteins." Biochem. Biophys. Res. Commun. 204: 1212–1218. Nov. 15, 1994.

Database EST, Accession No. R16683, Hillier L, et al., Unpublished. Apr. 14, 1995.

de Carvalho et al., "Regulation of Lysophospholipase Activity of the 85kDa Phospholipase $A_2$ and Activation in Mouse Peritoneal Macrophages", *J. Biol. Chem.* (1995) 270:20439–20446.

Fortes–Dias et al., "A Phospholipase $A_2$ Inhibitor from the Plasma of the South American Rattlesnake (*Crotalus durissus terrificus*)", *J. Biol. Chem.*, (1994) 269:15646–15651.

Gewert et al., "Dexamethasone down–regulates the 85 kDa phospholiphase $A_2$ in mouse macrophages and suppresses its activation", *Biochem. J.*, (1995), 307:499–504.

Jaattela et al., "Bcl–x and Bcl–2 inhibit TNF and Fas–induced apoptosis and activation of phospholiphase $A_2$ in breast carcinoma cells", *Oncogene*, (1995) 10:2297–2305.

Ross et al., "Characterization of a Novel Phospholipase $A_2$ Activity in Human Brain" *J. Neurochem.* (1995) 64:2213–2221.

Schalkwijk et al., "Epidermal growth factor (EGF) induces serine phosphorylation–dependent activation and calcium–dependent translocation of the cytosolic phospholipase $A_2$" *Eur. J. Biochem.* (1995) 231:593–601.

Tanaka et al., "Effect of thielocin $A1\beta$ on bee venom phospholipase $A_2$–induced edema in mouse paw" *Eur. J. Pharmacol.*, (1995) 279:143–148.

Trzeciak et al., "Effect of neuroleptics on phospholipase $A_2$ activity in the brain of rats" *Eur. Arch Psychiatry Clin Neurosci.*, (1995) 245:179–182.

Van den Berg et al., "Solution structure of porcine pancreatic phospholipase $A_2$" *EMBO J.*, (1995) 14:4123–4131.

Wijkander et al., "5–Lipoxygenase Products Modulate the Activity of the 85–kDa Phospholipase $A_2$ in Human Neutrophils" *J. Biol. Chem.*, (1995) 270:26543–26549.

Yamada et al., "Phospholipase $A_2$–Activating Peptide–Induced Contraction Of Smooth Muscle Is Mediated By Protein Kinase C–Map Kinase Cascade" *Biochem. Biophys Res. Commun.*, (1995) 217:203–210.

*Primary Examiner*—George C. Elliott
*Assistant Examiner*—Amy J. Nelson
*Attorney, Agent, or Firm*—Barbara J. Luther; Lucy J. Billings; Incyte Pharmaceuticals, Inc.

[57] ABSTRACT

The present invention provides a polynucleotide (gipl) the partial sequence for which was initially isolated from a THP-1 cDNA library and which identifies and encodes a novel human phospholipase inhibitor (GIPL). The invention provides for genetically engineered expression vectors and host cells comprising the nucleic acid sequence encoding GIPL.

5 Claims, 21 Drawing Sheets

```
                    9               18              27              36              45              54
5' NCA ATG GGC CGG CCG TGG GAA GGG TGA ATG TGG GTC CAG ACC CGC CCC TCC TCA 63              72              81              90              99             108
    GCT TCC TAT AAA AGC TGG GGA CCA GGT ACT GCT GAT ACA CAC ACC ATG AGG CTC
                                                                      M   R   L 117             126             135             144             153             162
    TCC AGG AGA CCA GAG ACC TTT CTG CTG GCC TTT GTG TTG CTC TGC ACC CTC CTG
    S   R   R   P   E   T   F   L   L   A   F   V   L   L   C   T   L   L 171             180             189             198             207             216
    GGT CTT GGG TGC CCA CTA CAC TGC GAA ATA TGT ACG GCG GCG GGG AGC AGG TGC
    G   L   G   C   P   L   H   C   E   I   C   T   A   A   G   S   R   C 225             234             243             252             261             270
    CAT GGC CAA ATG AAG ACC TGC AGC AGT GAC AAG GAC ACA TGT GTG CTC CTG GTC
    H   G   Q   M   K   T   C   S   S   D   K   D   T   C   V   L   L   V 279             288             297             306             315             324
    GGG AAG GCT ACT TCA AAG GGC AAG GAG TTG GTG CAC ACC TAC AAG GGC TGC ATC
    G   K   A   T   S   K   G   K   E   L   V   H   T   Y   K   G   C   I 333             342             351             360             369             378
    AGG TCC CAG GAC TGC TAC TCC GGC GTT ATA TCC ACC ACC ATG GGC CCC AAG GAC
    R   S   Q   D   C   Y   S   G   V   I   S   T   T   M   G   P   K   D 387             396             405             414             423             432
    CAC ATG GTA ACC AGC TCC TTC TGC TGC CAG AGC GAC GGC TGC AAC AGT GCC TTT
    H   M   V   T   S   S   F   C   C   Q   S   D   G   C   N   S   A   F 441             450             459             468             477             486
    TTG TCT GTT CCC TTG ACC AAT CTT ACT GAG AAT GGC CTG ATG TGC CCC GCC TGC
    L   S   V   P   L   T   N   L   T   E   N   G   L   M   C   P   A   C 495             504             513             522             531             540
    ACT GCG AGC TTC AGG GAC AAA TGC ATG GGG CCC ATG ACC CAC TGT ACT GGA AAG
    T   A   S   F   R   D   K   C   M   G   P   M   T   H   C   T   G   K
```

FIGURE 1A

```
       549          558          567          576          585          594
GAA AAC CAC TGC GTC TCC TTA TCT GGA CAC GTG CAG GCT GGT ATT TTC AAA CCC
 E   N   H   C   V   S   L   S   G   H   V   Q   A   G   I   F   K   P 603          612          621          630          639          648
AGA TTT GCT ATG CGG GGC TGT GCT ACA GAG AGT ATG TGC TTT ACC AAG CCT GGT
 R   F   A   M   R   G   C   A   T   E   S   M   C   F   T   K   P   G 657          666          675          684          693          702
GCT GAA GTA CCC ACA GGC ACC AAT GTC CTC TTC CTC CAT CAT ATA GAG TGC ACT
 A   E   V   P   T   G   T   N   V   L   F   L   H   H   I   E   C   T 711          720          729          738          747          756
CAC TCC CCC TGA AAA GCT ATC TGA ACA GAG GAA GAT AAT GTA GTG TGA AGT CCC
 H   S   P 765          774          783          792          801          810
CAT TTG TCC TCA GCC TGT AAC TTC CCC GTG TGC CTA TAA AGA AGT TAA TAG AGC 819          828          837
AAA AAA AAA AAA AAA AAA AAA AAC TCG AG 3'
```

FIGURE 1B

```
 1  N C A A T G G G C C G G C C G T G G G A A G G G T G A A T G  consensus
 1  - - - - - - - - - - - - - - - - - - - - - - - - - - - - - -  8941
 1  G - - - - - - - - - - - - - - - - - - - - - - - - - - - - -  10033
 1  G - - - - - - - - - - - - - - - - - - - - - - - - - - - - -  10644
 1  - - - - - - - - - - - - - - - - - - - - - - - - - - - - - -  10774
 1  - - - - - - - - - - - - - - - - - - - - - - - - - - - - - -  71854
 1  - - - - - - - - - - - - - - - - - - - - - - - - - - - - - -  72861
 1  - - - - - - - - - - - - - - - - - - - - - - - - - - - - - -  74452
 1  - - - - - - - - - - - C N T G G - - - - - - - - - - - - - -  155045
 1  N C A A T G G G C C G G C C G T G G G A A G G G T G A A T G  156817
 1  A G A A A G A G A C C A T N C C A G G A A - - G T - - - T G  619856
 1  - - - - - - - - - - - - - - - - - - - - - - - - - - - - - -  683480
 1  G - - - - - - - - - - - - - - G G A A - - - - - - - - - - -  1291208

31  T G G G T C C A G A C C C G C C C C T C C T C A G C T T C C  consensus
 1  - - - - - - - - - - - - - - - - - - - - - - - - - - - - - -  8941
 2  - - - - - - - - - - - - - - - - - - - - - - - - - - - - - -  10033
 2  - - - - - - - - - - - - - - - - - - - - - - - - - - - - - -  10644
 1  - - - - - - - - - - - - - - - - - - - - - - - - - - - - - -  10774
 1  - - - - - - - - - - - - - - - - - - - - - - - - - - - - - -  71854
 1  - - - - - - - - - - - - - - - - - - - - - - - - - - - - - -  72861
 1  - - - - - - - - - - - - - - - - - - - - - - - - - - - - - -  74452
 6  - - - - - - - - - - - - - - - - - C C T T A G T T T - -     155045
31  T G G G T C C A G A C C C G C C C C T C C T C A G C T T C C  156817
26  T G G G - - - - - - - - - - - - - - - - - - - - - - - - - -  619856
 1  - - - - - - - - - - - - - - - - - - - - - - - - - - - - - -  683480
 6  - - - - - - - - - - - - - - - - - T C C C A G - T T C T     1291208

61  T A T A A A A G C T G G G G A C C A G G T A C T G C T G A T  consensus
 1  - - - - - - - - - - - G G A - - - G G - - - - - - - - - - -  8941
 2  - - - - - - - - - - - - - - - - - - - - - - - - - - - - - -  10033
 2  - - - - - - - - - - - - - - - - - - - - - - - - - - - - - -  10644
 1  - - - - - - - - - - - - - - - - - - - - - - - - - - - - - -  10774
 1  - - - - - - - - - - - - - - - - - - - - - - - - - - - - - -  71854
 1  - - - - - - - - - - - - - - - - - - - - - - - - - - - - - -  72861
 1  - - - - - - - - - - - - - - - - - - - - - - - - - - - - - -  74452
15  - - - - - - - - - - - - - - - - - - - - - - - - - - - - - -  155045
61  T A T A A A A G C T G G G G A C C A G G T A C T G C T G A T  156817
30  - - - - - - - G T T G G G G A - - - G G - - - - - - - - - -  619856
 1  - - - - - - - - - - - - - - - - - - - - - - - - - - - - - -  683480
16  T G C A G C C A C T G G G A A T C A A G - - - - - - - - - -  1291208
```

FIGURE 2A

```
91   A C A C A C A C C A T G A G G C T C T C C A G G A G A C C A  consensus
 6   - - - - - - - - C C T A G G G T T - - - - - - A G G C - -    8941
 2   - - - - - - - - - - - - - - - - - - - - - - - - - - - - -   10033
 2   - - - - - - - - - - - - - - - - - - - - - - - - - - - - -   10644
 1   - - - - - - - - - - - - - - - - - - - - - - - - - - - - -   10774
 1   - - - - - - - - - - - - - - - - - - - - - - - - - - - - -   71854
 1   - - - - - - - - - - - - - - - - - - - - - - - - - - - - -   72861
 1   - - - - - - - - - - - - - - - - - - - - - - - - - - - - -   74452
15   - - - - - - - - - - - - - - - - - - - - - - - - - - - - -  155045
91   A C A C A C A C C A T G A G G C T C T C C A G G A G A C C A 156817
40   - - - - - - - - C C T A G G G T T - - - - - - A G G C - -  619856
 1   - - - - - - - - - - - - - - - - - - - - - - - - - - - - -  683480
36   - - - - - - - - - - - - - - - - - - - - - - - A G G C C C 1291208
```

FIGURE 2B

```
121  G A G A C C T T T C T G C T G G C C T T T G T G T T G C T C  consensus
 19  A A G A C C T T - - - - - - - - - - - - - - - - - - - - - -  8941
  2  - - - - - - - - - - - - - - - - - - - - - - - T T G C T C    10033
  2  - - - - - - - - - - - - - - - - - - - - - - - - - - - - - -  10644
  1  - - - - - - - - - - - C T G G C C T T T G T G T T G C T C    10774
  1  - - - - - - - - - - - C T - - - - - - - - - - - - - - - - -  71854
  1  - - - - - - - - - - - - - - - - - - - - - - - - - - - - - -  72861
  1  - - - - - - - - - - - - - - - - - - - - - - - - - - - - - -  74452
 15  - - - - - - - - - - - - - - - - - - - - - - - T N C N C      155045
121  G A G A C C T T T C T G C T G G C C T T T G T G T T G C T C  156817
 53  A A G A C C T T - - - - - - - - - - - - - - - - - - - - - -  619856
  1  - - - - - - - - - - - - - - - - - - - - - - - - - - - - - -  683480
 42  A A - - - - - - - - - - - - - - - - - - - - - - - C T C      1291208

151  T G C A C C C T C C T G G G T C T T G G G T G C C C A C T A  consensus
 27  - - - - - - - - - - - G A G G C A G G G G T - - - - - - - -  8941
  8  T N C A C C C T C C T G G G T C T T G G G T G C C C A C T A  10033
  2  - - - - - - - - - - - - - - - - - - - - - - - - - - - - - -  10644
 19  T G C A C C C T C C T G G G T C T T G G G T G C C C A C T A  10774
  3  - - - - - - - - - - - - - - - - - - - - - - - - - - - - - -  71854
  1  - - - - - - - - - - - - - - - - - - - - - - - - - - - - - -  72861
  1  - - - - - - - - - - - - - - - - - - - - - - - - - - - - - -  74452
 20  T - C A C C C T C C N G G G T C T N G G G T G C C C A C N A  155045
151  T G C A C C C T C C T G G G T C T T G G G T G C C C A C T A  156817
 61  - - - - - - - - - - - G A G G C A G G G G T - - - - - - - -  619856
  1  - - - - - - - - - - - - - - - - - - - - - - - - - - - - - -  683480
 47  C G - - - - - T C T T G - G T C T T N N N N N N N N N N N N  1291208

181  C A C T G C G A A A T A T G T A C G G C G G C G G G G A G C  consensus
 38  - - - - - T G A A G C - - - - - - - - - - - C A G G G A G -  8941
 38  C A C T G C G A A A T A T G T A C G G C G G C G G G G A G C  10033
  2  - - - - - - - - - - - - - - - - - - - - - - - - - - - - - -  10644
 49  C A C T G C G A A A T A T G T A C G G C G G C G G G G A G C  10774
  3  - - - - - - - - - - - - - - - - - - - - - - - - - - - - - -  71854
  1  - - - - - - - - - - - - - - - - - - - - - - - - - - - - - -  72861
  1  - - - - - - - - - - - - - - - - - - - - - - - - - - - - - -  74452
 49  C A C T G C G A A N T A T G T A C G G C G G C G G G T A G C  155045
181  C A C T G C G A A A T A T G T A C G G C G G C G G G G A G C  156817
 72  - - - - - T G A A G C - - - - - - - - - - - C A G G G A G -  619856
  1  - - - - - - - - - - - - - - - - - - - - - - - - - - - - - -  683480
 71  N N N N N N N C A A T G G G C - C G G C C G T G G G A A G -  1291208
```

FIGURE 2C

```
211 A G G T G C C A T G G C C A A A T G A A G A C C T G C A G C  consensus
 51 - - - - - - - T G G T C A G C - - - - - - - - - - C A G C  8941
 68 A G G T G C C A T G G C C A A A T G A A G A C C T G C A G C  10033
  2 - - - - - - - - - - - - - - - - - - - - - - - - - - - -  10644
 79 A G G T G C C A T G G C C A A A T G A A G A C C T G C A G C  10774
  3 - - - - - - - - - - - - - - - - - - - - - - - - - - - -  71854
  1 - - - - - - - - - - - - - - - - - - - - - - - - - - - -  72861
  1 - - - - - - - - - - - - - - - - - - - - - - - - - - - -  74452
 79 A G G T T C C A T G N C C A A A T N A A G A N C T T C A N C  155045
211 A G G T G C C A T G G C C A A A T G A A G A C C T G C A G C  156817
 85 - - - - - - - T G G T C A G C - - - - - - - - - - C A G C  619856
  1 - - - - - - - - - - - - - - - - - - - - - - - - - - - -  683480
 99 - G G T G - - - - - - - - - - A A T G T G G G T C - - C A G -  1291208
```

FIGURE 2D

```
241 A G T G A C A A G G A C A C A T G T G T G C T C C T G G T C   consensus
 63 A C T G T C - - - - - - - C C T G C C T G T C C C C A - T C   8941
 98 A G T G A C A A G G A C A C A T G T G T G C T C C T G G T C   10033
  2 - - - - - - - - - - A C A C A T G T G T N C T C C T G G T C   10644
109 A G T G A C A A G G A C A C A T G T G T G C T C C T G G T C   10774
  3 - - - - - - - - - - - - - - - - - - - - - - - - - - - - - -   71854
  1 - - - - - - - - - - - - - - - - - - - - - - - - - - - - - -   72861
  1 - - - - - - - - - - - - - - - - - - - - - - - - - - - - - -   74452
109 N G T G A C A A G G A C A C A T G T N T G C T C C T G G T C   155045
241 A G T G A C A A G G A C A C A T G T G T G C T C C T G G T C   156817
 97 A C T G T C - - - - - - - C C T G C C T G T C C C C A - T C   619856
  1 - - - - - - - - - - - - - - - - - - - - - - - - - - - - - -   683480
116 - - - - - - - - - - - - - - - A C C C G C C C C T C C T C   1291208

271 G G G A A G G C T A C T T C A A A G G G C A A G G A G T T G   consensus
 85 - - - - - - - C C A - - - C A G A G G G C A A G G A G T T G   8941
128 G G G A A G G C T A C T T C A A A G G G C A A G G A G T T G   10033
 22 G G G A A G G C T A C T T C A A A G G G C A A G G A G T T G   10644
139 G G G A A G G C T A C T T C A A A G G G C A A G G A G T T G   10774
  3 - - - - - - - - - - - - - - - - - - - - - - - - - - - - - -   71854
  1 - - - - - - - - - - T - - - - - - - - - - - - - - - - T T G   72861
  1 - - - - - - - - - - - - - - - - - - - - - - - - - - - - - -   74452
139 G G N A A G N C T A C T T C A A A G G G C A A G G A G T T G   155045
271 G G G A A G G C T A C T T C A A A G G G C A A G G A G T T G   156817
119 - - - - - - - C C A - - - C A G A G G G C A A G G A G T T G   619856
  1 - - - - - - - - - - - - - - - - - - - - - - - - - - G T T G   683480
130 A G - - - - - - - C T T C - - - - - - - - - - - - - - - - -   1291208

301 G T G C A C A C C T A C A A G G G C T G C A T C A G G T C C   consensus
105 G T G C A C A C C T A C A A G G G C T G C A T C A G G T C C   8941
158 G T G C A C A C C T A C A A G G G C T G C A T C A G G T C C   10033
 52 G T G C A C A C C T A C A A G G G C T G C A T C A G G T N C   10644
169 G T G C A C A C C T A C A A G G G C T G C A T C A G G T C C   10774
  3 - - - - - - - - - - - - - - - - - - - - - - - - - - - - - -   71854
  5 G T G C A C A C C T A C A A G G G C T G C A T C A G G T C C   72861
  1 - - - - - - - - - - - - - - - - - - - - - - - - - - - - - -   74452
169 G T G C A C                                                   155045
301 G T G C A C A C C T A C A A G G G C T G C A T C A G G T C C   156817
139 G T G C A C A A C T A C A A G G G C T G C A T C A G G T C C   619856
  5 G T G C A C A C C T A C A A G G G C T G C A T C A G G T C C   683480
136 - - - - - - - C T A T A A A A G C T G - - - - - - - - - - -   1291208
```

FIGURE 2E

```
331 C A G G A C T G C T A C T C C G G C G T T A T A T C C A C C  consensus
135 C A G G A C T G C T A C T C C G G C G T T A T A T C C A C C  8941
188 C A G G A C T G C T A C T C C G G C G T T A T A T C N A C C  10033
82  C A G G A C T G C T A C T C C G G C G T T A T A T C C A C C  10644
199 C A G G A C T G C T A C T C C G G N G T T A T A T C C A C C  10774
3   - - - - - - - - - - C C G G C G T T A T A T C C A C C  71854
35  C A G G A C T T C T A C T C C G G C G T T A T A T C C A C C  72861
1   - - - - - - - - - - C T C C G G N G T T A T A T C C A C C  74452
174                                                              155045
331 C A G G A C T G C T A C T C C G G C G T T A T A T C C A C C  156817
169 C A G G A C T G C T A C T N C G G N G T T A T A T C C A C C  619856
35  C A G G A C T G C T A C T C C G G C G T T A T A T N C A C C  683480
148 - - - - - - - - - - - - - - - - - - - - - - - - - - -  1291208
```

FIGURE 2F

```
361 A C C A T G G G C C C C A A G G A C C A C A T G G T A A C C  consensus
165 A C C A T G G G C C C C A A G G A C C A C A T G G T A A C C  8941
218 A C C A T G G G C C C C A A G G A C C A C A T G G T A A C C  10033
112 A C C A T G G G C C C C A A G G A C C A C A T G G T A A C C  10644
229 A C C A T G G G C C C C A A G G A C C A C A T G G T A A C C  10774
 20 A C C A T G G G C C C C A A G G A C C A C A T G G T A A C C  71854
 65 A C C A T G G G C C C C A A G G A C C A C A T G G T A A C C  72861
 20 A C C A T G G G C C C C A A G G A C C A C A T G G T A A C C  74452
174                                                              155045
361 A C C A T G G G C C C C A A G G A C C A C A T G G T A A C C  156817
199 A C C A T G G G C C C C A A G G A C C A C A T G G T         619856
 65 A C C A T G G G N C C C A A G G A C C A C A T G G T A A C C  683480
148 - - - - - - - - - - - - - G G G A C C A - - - G G T A - - -  1291208

391 A G C T C C T T C T G C T G C C A G A G C G A C G G C T G C  consensus
195 A G C T C C T T C T G N T G C C A G A G C G A C G G C T G C  8941
248 A G C T C C T T C T G C T G C - A G A G C G A C G G C T G C  10033
142 A G C T C C T T C T G C T G C C A G A G C G A C G G C T G C  10644
259 A G C T C C T T C T G C T G C C A G A G C G A C G G C T G C  10774
 50 A G C T C C T T C T G C T G C C A G A G C G A C G G C T G C  71854
 95 A G C T C C T T N T G C T G C C A G A G C G A C G G C T G C  72861
 50 A G C T C C T T C T G C T G C C A G A G C G A C G G C T G C  74452
174                                                              155045
391 A G C T C C T T C T G C T G C C A G A G C G A C G G C T G C  156817
224                                                              619856
 95 A G C T C C T T N T G C T G C C A G A G C G A C G N C T G C  683480
159 - - - - - - - - - - - - - - - - - - - - - - - C T G C        1291208

421 A A C A G T G C C T T T T T G T C T G T T C C C T T G A C C  consensus
225 A A C A G T G C C T T T T T G T C T G T T C C C T T G A C C  8941
277 A A C A G T G C C T T T T T G T C T G T T C C C T T G A C C  10033
172 A A C A G T G C C T T T T T G T C T G T T C C C T T G A C C  10644
289 A A C A G T G C C T T T T T G T C T G T T C C C T T G A C C  10774
 80 A A C A N T G C C T T T T T N T N T G T T C C C T T G A C C  71854
125 A A C A T T G C C T T T T T N T N T G T N C C C T T G        72861
 80 A A C A N T G C C T T T T T N T N T G T T C C C T T G A C C  74452
174                                                              155045
421 A A C A G T G C C T T T T T G T C T G T T C C C T T G A C C  156817
224                                                              619856
125 A A C A G T G C C T T T T T G T C T G T T C C C T T G A C C  683480
163 - - - - - - - - - - - - - - - - - - - - - - - - - - - - -    1291208
```

FIGURE 2G

```
451 A A T C T T A C T G A G A A T G G C C T G A T G T G C C C C  consensus
255 A A T C T T A C T G A G A A T G G C C T G A T G T G C C C N  8941
307 A A T C T T A C T G A G A A T G G T                          10033
202 A A T N T T A C T G A G A A T N G N C T G A T G T G C C C C  10644
319 A A T C T T A C T G A G A A T G G C C T G A T G T G C C C C  10774
110 A A T C T T A C T G A G A A T G G C C T G A T G T G C C C C  71854
151                                                              72861
110 A A T C T T A C T G A G A A T G G C C T G A T G T G C C C C  74452
174                                                              155045
451 A A T C T T A C T G A G A A T G G C C T G A T G T G C C C C  156817
224                                                              619856
155 A A T C T T A C T G A G A A T G G C C T G A T G T G C C C C  683480
163 - - - - - - - - - - - - - - - - - - T G A T A C A C - - -    1291208
```

FIGURE 2H

```
481 G C C T G C A C T G C G A G C T T C A G G G A C A A A T G C  consensus
285 G C - T G C A C T G C G A G T T T N A G G G N C A A - - -    8941
324                                                              10033
232 G N C T G C A C T G N G A G C T T C A G G G A C A A A T G C  10644
349 G C C T G C A C T G C G A G C T T C A G G G A C A A A T G C  10774
140 G C C T G C A C T G C G A G C T T C A G G G A C A A A T G C  71854
151                                                              72861
140 G C C T G C A C T G C G A G C T T C A G G G A C A A A T G C  74452
174                                                              155045
481 G C C T G C A C T G C G A G C T T C A G G G A C A A A T G C  156817
224                                                              619856
185 G N C T G C A C T G C G A G C T T N A G G G A C A A A T G C  683480
171 - - - - A C A C - - - - - - - - - - - - - - - - - - - - C    1291208

511 A T G G G G C C C A T G A C C C A C T G T A C T G G A A A G  consensus
311 - - - - - A T N C A T G - - - - - - - - - - - - - - - - -    8941
324                                                              10033
262 - - - - - - - - - - - - - - - - - - - - - - - - - - - -      10644
379 A T G G G G C C C A T G A C C C A C T G T A C T G G A A A G  10774
170 A T G G G G C C C A T G A C C C                              71854
151                                                              72861
170 A T G G G G C C C A T G A C C C - - - - - - C A G G A - - -  74452
174                                                              155045
511 A T G G G G C C C A T G A C C C A C T G T A C T G G A A A G  156817
224                                                              619856
215 A T G G G G C C C A T G A C C C A C T G T A C T G G A G A G  683480
176 A T G A G G C T C - - - - T C C A - - - - - - - - - - - -    1291208

541 G A A A A C C A C T G C G T C T C C T T A T C T G G A C A C  consensus
318 - - - - - - - - - - - - - - - - - - - - - - - - - - - - -    8941
324                                                              10033
262 - - - - - - - - - - - - - - - - - - - - - - - - - - - -      10644
409 G A A A A C C A C T G C G T C T C C T T A T G T G G A C A C  10774
185                                                              71854
151                                                              72861
191 - - - - - - - - C T G C - - - - - - - - - - - - - - - - -    74452
174                                                              155045
541 G A A A A C C A C T G C G T C T C C T T A T C T G G A C A C  156817
224                                                              619856
245 G A A A A C C A                                              683480
189 G G A G A C C A - - - - - - - - - - - - - - - - - G A G A C  1291208
```

FIGURE 21

```
571  G T G C A G G C T G G T A T T T T C A A A C C C A G A T T T  consensus
318  - - - - - - - - - - - - - - - - - - - - - - - - - - - -      8941
324                                                                10033
262  - - - - - - - - - - - - - - - - - - - - - - - - - - - -      10644
439  G T G C A T G C T G G T A T T T T C A A A C C C A G A T T T  10774
185                                                                71854
151                                                                72861
195  - - - - - - - - - - T A C T C - - - - - - - - - - - - - -    74452
174                                                                155045
571  G T G C A G G C T G G T A T T T T C A A A C C C A G A T T T  156817
224                                                                619856
252                                                                683480
202  - - - - - - - - - - - C T T T C - - - - - - - - - - - - T    1291208
```

FIGURE 2J

```
601 G C T A T G C G G G G C T G T G C T A C A G A G A G T A T G  consensus
318 - - - - - - G G G G - - - - - - - - - - - - - - - - - - - -  8941
324                                                              10033
262 - - - - - - - - - - - - - - - - - - - - - - - - - - - - T    10644
469 G C T A T G C G G G G C T G T G C T A C A G A G A G T A T G  10774
185                                                              71854
151                                                              72861
200 - - - - - - C G G N G T T A T A - - - - - - - - - - - - - -  74452
174                                                              155045
601 G C T A T G C G G G G C T G T G C T A C A G A G A G T A T G  156817
224                                                              619856
252                                                              683480
208 G C T - - - - - - G G C - - - - - - - - - - - - - - - - - -  1291208

631 T G C T T T A C C A A G C C T G G T G C T G A A G T A C C C  consensus
322 - - - - - - - - - - - - - - - - - - - - - - - - - - - - - -  8941
324                                                              10033
262                                                              10644
499 T G C T T T A C C A A G C C T G G T G C T G A A G T A C C C  10774
185                                                              71854
151                                                              72861
210 - - - T C C A C C A - - - - - - - - - - - - - - - - - C C    74452
174                                                              155045
631 T G C T T T A C C A A G C C T G G T G C T G A A G T A C C C  156817
224                                                              619856
252                                                              683480
214 - - C T T T - - - - - - - - - G T G T T G - - - - - - - - -  1291208

661 A C A G G C A C C A A T G T C C T C T T C C T C C A T C A T  consensus
322 - - - - - - - - - - - - - - - - - - - - - - - - - - - - - -  8941
324                                                              10033
262                                                              10644
529 A C A G G C A C C A A T G T C C T C T T C C T C C A T C A T  10774
185                                                              71854
151                                                              72861
219 A T G G G C C C C A A G G - - - - - - - - - - - - A C C A C  74452
174                                                              155045
661 A C A G G C A C C A A T G T C C T C T T C C T C C A T C A T  156817
224                                                              619856
252                                                              683480
224 - - - - - - - - - - - - - - - - - - - - C T C - - - - - -    1291208
```

FIGURE 2K

```
691 A T A G A G T G C A C T C A C T C C C C C T G A A A A G C T  consensus
322 - - - - - - - - - - - - - - - - - - - - - - - - - - - - - -  8941
324                                                              10033
262                                                              10644
559 A T A G A G T G C A C T C A C T C C C C C T G A A A A G C T  10774
185                                                              71854
151                                                              72861
237 A T G - - G T A - A C C A G C T C C T T C T G - - - - - C T  74452
174                                                              155045
691 A T A G A G T G C A C T C A C T C C C C C T G A A A A G C T  156817
224                                                              619856
252                                                              683480
227 - - - - - - T G C A C - - - - - C C T C C T G G G - - - - -  1291208
```

FIGURE 2L

```
721 A T C T G A A C A G A G G A A G A T A A T G T A G T G T G A  consensus
322 - - - - - - - - - - - - - - - - - - - - - - - - - - - - - -  8941
324                                                              10033
262                                                              10644
589 A T C T G A A C A G A G G A A G A T A A T G T A G T G T G A  10774
185                                                              71854
151                                                              72861
259 G C C A G A G C N A C G G C - - - - - T G C A A C - - - -   74452
174                                                              155045
721 A T C T G A A C A G A G G A A G A T A A T G T A G T G T G A  156817
224                                                              619856
252                                                              683480
241 - - - - - - - - - - - - - - - - - - - - - - - - - - - - - -  1291208

751 A G T C C C C A T T T G T C C T C A G C C T G T A A C T T C  consensus
322 - - - - C C C A T T                                          8941
324                                                              10033
262                                                              10644
619 A G T C C C C A T T T G T T C C T A G N C T G T A A C T T C  10774
185                                                              71854
151                                                              72861
279 A N T G C C - - T T T N T - - - - - G T C T G T N - - - - C  74452
174                                                              155045
751 A G T C C C C A T T T G T C C T C A G C C T G T A A C T T C  156817
224                                                              619856
252                                                              683480
241 - - - - - - - - - - - - T C T T G G - - - - - - - - - - -    1291208

781 C C C G T G T G - C C T A T A A A G A A G T T A A T A G A G  consensus
327                                                              8941
324                                                              10033
262                                                              10644
649 C C - G T G T G G C C T A T A A N G A A G T T A A T N G N G  10774
185                                                              71854
151                                                              72861
298 C C T - - - T G A C C - - - - - - - A A T C T N A C T G A G  74452
174                                                              155045
781 C C C G T G T G - C C T A T A A A G A A G T T A A T A G A G  156817
224                                                              619856
252                                                              683480
247 - - - G T G C                                                1291208
```

FIGURE 2M

```
810  C A A A A A A A A A A A A A A A A A A A A A A C T C G A G  consensus
327                                                             8941
324                                                             10033
262                                                             10644
678  C A A A N N A N A A A G A A A A A A A                      10774
185                                                             71854
151                                                             72861
318  - - - - - - - - - - - - - - - - - A A T N G C C T G A T T  74452
174                                                             155045
810  C A A A A A A A A A A A A A A A A A A A A A A C T C G A G  156817
224                                                             619856
252                                                             683480
250                                                             1291208
```

FIGURE 2N

```
1    M R L S R R P E T F L L A F V L L C T L L G L G C P L H C E      GIPL aa
1    M K - - - - - - Y L H T I C L L F I F V A R G N S R S C D      CNF aa

31   I C T A A G S R C H G Q M K T C S S D K D T C V L L V G K A    GIPL aa
24   F C H N I G K D C D G Y E E E C S S P E D V C G K V L L E I    CNF aa

61   T S K G K E L V H T Y K G C I R S Q D C Y S G V I S T T M G    GIPL aa
54   S S A S L S V R T V H K N C F S S S I C K L G Q F D V N I G    CNF aa

91   P K D H M V T S S F C C Q S D G C N S - A F L S V P L T N L    GIPL aa
84   H H S Y I R G R I N C C E K E L C E D Q P F P G L P L S K -    CNF aa

120  T E N G L M C P A C T A S F R D K C M G P M T H C T G K E N    GIPL aa
113  - P N G Y Y C P G A I G L F T K D S T E Y E A I C K G T E T    CNF aa

150  H C V S L S G H V Q A G I F K P - - R F A M R G C A T E S M    GIPL aa
142  K C I N I V G H - R Y E Q F P G D I S Y N L K G C V S S - -    CNF aa

178  C F T K P G A E V P T G T N V L F L H H I E C T H S P          GIPL aa
169  C P L L S L S N A T F E Q N R N Y L E K V E C K D A I R L A    CNF aa

204                                                                 GIPL aa
199  S L                                                           CNF aa
```

FIGURE 3

HUMAN PHOSPHOLIPASE INHIBITOR

CROSS-REFERENCE TO RELATED APPLICATIONS

This application is a continuation-in-part of U.S. patent application Ser. No. 08/644,754, entitled Human Phospholipase Inhibitor, filed May 10, 1996.

FIELD OF THE INVENTION

The present invention relates to nucleic acid and amino acid sequences of a novel human phospholipase inhibitor and to the use of these sequences in the diagnosis, study, prevention and treatment of disease.

BACKGROUND OF THE INVENTION

Phospholipase enzymes catalyze the removal of fatty acid residues from phosphoglycerides. Specifically, phospholipase A2 (PLA2) cleaves the ester bond at the 2 position of the glycerol moiety of membrane phospholipids giving rise to equimolar amounts of arachidonic acid and lysophospholipids. Although PLA2 preferentially cleaves arachidonic acid from phospholipids, arachidonic acid is generated secondarily from intermediates of the S1, phospholipase C- and phospholipase D-activated pathways.

Although the known PLA2s were originally divided into groups by source organism, shown in parentheses, and their primary amino acid sequences, they are now characterized by a growing list of other attributes. Group 1 includes the 80–90 kD PLA2s (mammalian) which are active at pH 6–8 and dependent on the presence of calcium ion ($Ca^{++}$). Group II is a mixture of approximately 14 kD, secreted PLA2s (snake) which bind heparin and are inhibited by dexamethadone, dithiothreitol and deoxycholate. Group III is the cytosolic, 100 kD PLA2s (honey bee venom). The prokaryotic versions of PLA2 are produced by bacteria such as *Streptomyces violaceoruber*.

Several recent scientific studies reveal pertinent facts towards the characterization of PLA2s and their lipolytic activity. Van den Berg B et al. (1995; EMBO J 14:4123–31) reported that PLA2 appears to be more active in the degradation of high molecular weight aggregates than of monomers. In vitro experiments by de Carvalho M G et al. (1995; J Biol Chem 270:20439–46) showed that with a bilayer substrate, PLA2 preferentially and sequentially deacylates sn-2 and then sn-1 acyl groups. Ross et al. (1995; J Neurochem 64:2213–21) reported that in the temporal cortex of the human brain, PLA2 activity was higher in membrane fraction than in the cytosolic fraction.

Arachidonic acid, the product of PLA2 activity, is processed into bioactive lipid mediators such as lyso-platelet-activating factor (lyso-PAF) or shuttled into pathways for the synthesis of eicosanoids. In fact the release of arachidonic acid from membrane phospholipids is the rate-limiting step in the biosynthesis of the four major classes of eicosanoids (prostaglandins, prostacyclins, thrombosanes and leukotrienes) involved in pain, fever, and inflammation. Furthermore, leukotriene-B4 (LKB4) is known to function in a feedback loop which induces further increased PLA2 activity.

PLA2 has many other known activators which include tumor necrosis factor (Jaattela M et al. (1995) Oncogene 10:2297–305); the protein phosphatase inhibitor, okadaic acid (Gewert K and R Sundler (1995) Biochem J 307:499–504); the neuroleptics, fluphenazine and thioridazine (Trzeciak H I et al (1995) Eur Arch Psychiatry Clin Neurosci 245:179–182); the mammalian phospholipase A2-activating protein (PLAP; Yamada H and Bitar KN (1995) Biochem Biophys Res Commun 217:203–10); and the eicosanoids, LKB4, 5-oxoeicosatetraenoic acid, or 5-hydroxyeicosatetraenoic acid (Wijkander J et al (1995) J Biol Chem 270:26543–9). Epidermal growth factor specifically induces serine phosphorylation-dependent and calcium-dependent activation of cytosolic PLA2 (Schalkwijk C G et al. (1995) Eur J Biochem 231:593–601).

Inhibitors of PLA2 are useful in the regulation of the signaling cascades that result from or correlate with PLA2 activity. One pronounced example of this signaling is seen in sepsis where the increase in PLA2 was found to be more than 12,000-fold normal and PLA2 was associated with complement C3-derived anaphylatoxin. PLA2 inhibitors include chemical molecules such as p-bromophenacyl bromide and biological molecules such as the specific inhibitor, thielocin A1 beta, produced by a fungus (Tanaka et al. (1995) Eur J Pharmacol 279:143–8) and nonspecific inhibitors such as glucocorticoids.

Fortes-Dias C L et al. (1994; J Biol Chem 269:15646–51) have isolated and characterized a PLA2 inhibitor from the plasma of a South American rattlesnake, *Crotalus durissus terrificus*. This 20–24 kD protein, designated Crotalus neutralizing factor (CNF), appears to self-associate as a 6–8 oligomeric aggregate. The crotoxin molecule which CNF neutralizes is active only as a dimer and consists of an acidic molecule (CA) associated with one of two basic isoforms of PLA2 ($CB_1$ and $CB_2$). CNF actually displaces CA to form a stable association with one of the CB molecules. This displacement inactivates the neurotoxic, cardiotoxic, myotoxic, anticoagulent and platelet-activating activities of crotoxin.

The full length 840 bp cDNA of CNF was cloned from Crotalus liver tissue. The nucleotide sequence encodes a 19 residue signal peptide and a 181 residue mature protein with 16 cysteines, a pI of 5.45, and a possible glycosylation site at $N_{157}$. Fortes-Dias states that the cDNA contains noncoding sequence and lacks a putative polyadenylation site. In inhibitory assays, the acidic CNF molecule also inhibits the activity of bee venom, and in 100-fold excess in plasma, porcine pancreatic PLA2.

SUMMARY

The present invention relates to a novel phospholipase inhibitor initially identified among the partial cDNAs from a THP-1 cell library and to the use of the nucleic acid and amino acid sequences in the study, diagnosis, prevention and treatment of disease.

The phospholipase inhibitor of the present invention was first identified within Incyte Clone 156817 through a computer generated search for amino acid sequence alignments. The nucleic acid sequence, SEQ ID NO: 1, disclosed herein and designated in lower case, gipl, encodes the amino acid sequence, SEQ ID NO: 2, designated in upper case, GIPL. The present invention is based, in part, on the chemical and structural homology between GIPL and Crotalus phospholipase A2 inhibitor, CNF (GenBank GI 501050; Fortes-Dias C L et al. 1994; J Biol Chem 269:15646–51).

GIPL has 23% identity to the mature CNF molecule, and lacks homology to any other nucleotide or protein sequence in GenBank. GIPL is 204 amino acids long and lacks potential N-linked glycosylation sites. It contains 19 cysteine residues, 16 of which align with the cysteine residues of the mature CNF. The nucleic acid sequence, oligonucleotides, fragments, portions or antisense molecules thereof, may be used in diagnostic assays of body fluids or biopsied tissues to detect the expression level of gipl. For example, gipl sequences designed from the consensus sequence or the contiguous sequences found in Incyte Clones 8491, 10033, 10644, 10774, 72861, 74452, 75814, 155045, 156817, 619856, 683480 and 1291208 (SEQ ID NOs: 4–15) can be used to detect the presence of the mRNA transcripts in a patient or to monitor the decrease in transcripts during treatment.

The nucleic acid sequence also provides for the design of antisense molecules useful in diminishing or eliminating expression of the genomic nucleotide sequence in individuals in which normal or increased phospholipase activity would ameliorate disease. The present invention also relates, in part, to the inclusion of the polynucleotide in an expression vector which can be used to transform host cells or organisms. Such transgenic hosts are useful for production of GIPL.

The invention further provides diagnostic kits for the detection of naturally occurring GIPL. It provides for the use of purified GIPL to produce antibodies or to use in the identification of agonists which induce GIPL or antagonists or inhibitors which bind GIPL. Such agonists, antagonists or inhibitors can be delivered into the vascular system, lymph or cerebrospinal fluid to interact with GIPL and alter the activity of phospholipases. Anti-GIPL antibodies are useful in inhibition of GIPL and to monitor GIPL activity in biopsied tissues where GIPL is expressed.

The invention comprises pharmaceutical compositions comprising the protein, antisense molecules capable of disrupting expression of the native gene, and agonists, antibodies, antagonists or inhibitors of the disclosed protein. These compositions are useful for the prevention or treatment of conditions such as viral, bacterial or fungal infections including septic and toxic shock and gangrene; autoimmune responses encompassing but not limited to anemias, asthma, systemic lupus, and myasthenia gravis; hereditary or cancerous conditions such as Alzheimer's, breast carcinoma, diabetes mellitus, osteoporosis, and schizophrenia; glomerulonephritis; pregnancy; rheumatoid and osteoarthritis; scleroderma; and insect or snake bites or stings in which phospholipases are a component of the injected venom.

DESCRIPTION OF THE FIGURES

FIGS. 1A and 1B display the nucleic acid sequence (SEQ ID NO: 1) and deduced amino acid sequence (SEQ ID NO: 2) of the phospholipase inhibitor, GIPL, originally identified among the partial cDNAs from a THP-1 library (THP1PLB02). The alignment of the nucleic acid and amino acid sequences was produced using MacDNAsis software (Hitachi Software Engineering Co Ltd).

FIGS. 2A–2N show the nucleic acid sequence alignment of the consensus sequence (SEQ ID NO: 1) with the the partial cDNAs, Incyte Clones 8491, 10033, 10644, 10774, 72861, 74452, 75814, 155045, 156817, 619856, 683480, and 1291208 (SEQ ID NOs: 4–15). Sequences were aligned using the multisequence alignment program of DNAStar software (DNAStar Inc, Madison Wis.).

FIG. 3 shows the amino acid sequence alignments between the consensus translation for GIPL (SEQ ID NO: 2), and Crotalus neutralizing factor, CNF (GI 501050; Fortes-Dias C L et al. (1994) J Biol Chem 269:15646–51). Sequences were aligned using the multisequence alignment program of DNAStar software (DNAStar Inc, Madison Wis.).

DETAILED DESCRIPTION OF THE INVENTION

Figure 4:
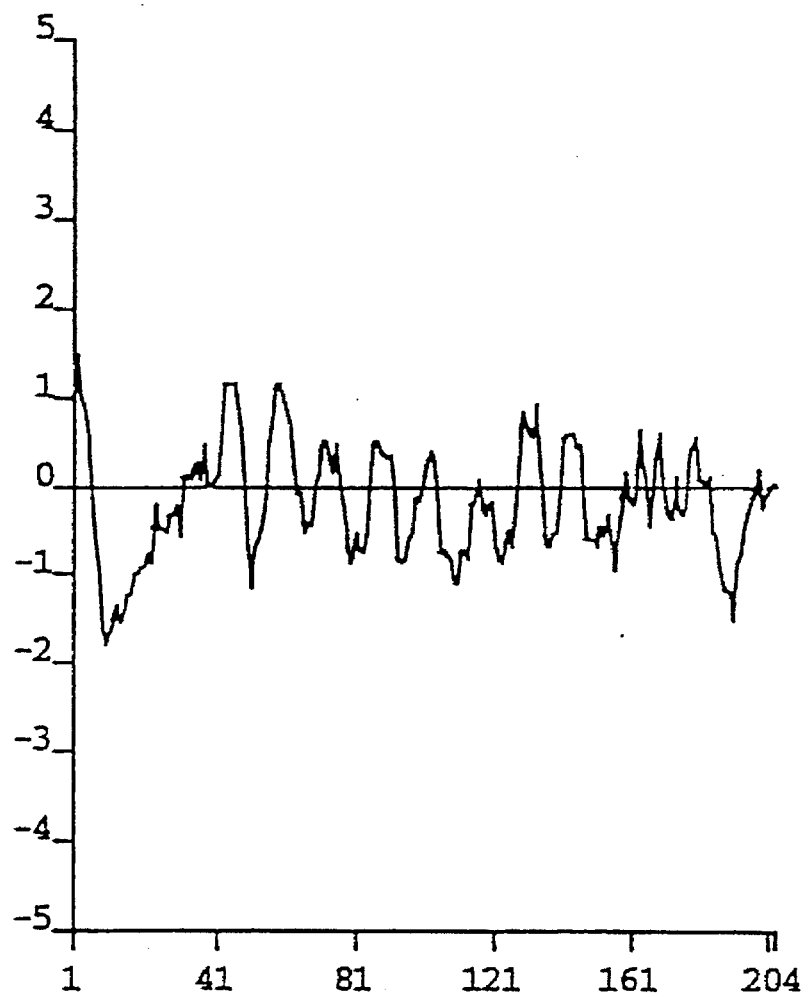
FIG. 4 shows the hydrophobicity plot for GIPL. The X axis reflects amino acid position, and the negative Y axis, hydrophobicity. The hydrophobicity plot was generated using MacDNAsis software.

The present invention relates to a novel phospholipase inhibitor, the partial nucleic acid sequence for which was initially identified in Incyte Clone 156817 from a cDNA library (THP1PLB02) prepared from phorbol and lipopolysaccharide stimulated THP-1 cells and to the use of the polynucleotide (lower case, gipl; SEQ ID NO: 1) and polypeptide (upper case, GIPL; SEQ ID NO: 2) shown in FIG. 1 in the study, diagnosis, prevention and treatment of disease. The present invention is based, in part, on the chemical and structural homology between the mature proteins of GIPL and Crotalus phospholipase A2 inhibitor, CNF (GenBank GI 501050; Fortes-Dias C L et al. 1994; J Biol Chem 269:15646–51).

GIPL has 23% identity to the known mature CNF molecule, and lacks statistically significant homology to any other nucleotide or protein sequence in GenBank. GIPL is 204 amino acids long and lacks potential N-linked glycosylation sites. However, it contains 19 cysteine residues, 16 of which align with the cysteine residues of CNF.

The nucleic acid sequence, oligonucleotides, fragments, portions or antisense molecules thereof, may be used in diagnostic assays of body fluids or biopsied tissues to detect the expression level of gipl. For example, gipl sequences designed from the consensus sequence SEQ ID NO: 1 or the related sequences found in Incyte Clones 8491 (SEQ ID NO: 4, from cDNA library HMC1NOT01), 10033 (SEQ ID NO: 5, from cDNA library THP1PLB01), 10644 (SEQ ID NO: 6, from cDNA library THP1PLB01), 10774 (SEQ ID NO: 7, from cDNA library THP1PLB01), 72861 (SEQ ID NO: 8, from cDNA library THP1PEB01), 74452 (SEQ ID NO: 9, from cDNA library THP1PEB01), 75814 ((SEQ ID NO: 10, from cDNA library THP1PEB01), 155045 (SEQ ID NO: 11, from cDNA library THP1PIB02), 156187 (SEQ ID NO: 12, from cDNA library THP1PIB02), 619856 (SEQ ID NO: 13 from cDNA library PGANNOT01), 683480 (SEQ ID NO: 14 from cDNA library UTRSNOT02) and 1291208 (SEQ ID: 15 from cDNA library BRAINOT11) can be used to detect the presence of the mRNA transcripts or to monitor the changes in the number of transcripts in a patient's cells or tissues during treatment.

The nucleic acid sequence also provides for the design of antisense molecules useful in diminishing or eliminating expression of the inhibitory genomic nucleotide sequence. In individuals with Alzheimer's, the maintenance of normal phospholipase activity could slow down progression of the disease. The present invention also relates, in part, to the inclusion of the polynucleotide in an expression vector which can be used to transform host cells or organisms. Such transgenic hosts are useful for production of GIPL.

The invention further provides diagnostic kits for the detection of naturally occurring GIPL. It provides for the use of purified GIPL to produce antibodies or to use in the identification of agonists which induce GIPL or antagonists or inhibitors which bind GIPL. Such agonists, antagonists or inhibitors can be delivered into the vascular system, lymph or cerebrospinal fluid to bind with GIPL and influence the activity of phospholipases. Anti-GIPL antibodies are useful in inhibition of GIPL and to monitor GIPL activity in biopsied tissues where GIPL is expressed.

The invention comprises pharmaceutical compositions comprising the protein, antisense molecules capable of disrupting expression of the genomic sequence, and agonists, antibodies, antagonists or inhibitors of the disclosed protein. These compositions are useful for the prevention or treatment of conditions such as viral, bacterial or fungal infections including septic and toxic shock and gangrene; autoimmune responses encompassing but not limited to anemias, asthma, systemic lupus, and myasthenia gravis; hereditary or cancerous conditions such as Alzheimer's, breast carcinoma, diabetes mellitus, osteoporosis, and schizophrenia; glomerulonephritis; pregnancy; rheumatoid and osteoarthritis; scleroderma; and insect or snake bites or stings in which phospholipases are a component of the injected venom.

The nucleotide sequences encoding GIPL (or its complement) have numerous applications in techniques known to those skilled in the art of molecular biology. These techniques include use as hybridization probes, use as oligomers for PCR, use for chromosome and gene mapping, use in the recombinant production of GIPL, and use in generation of antisense DNA or RNA, their chemical analogs and the like. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

It will be appreciated by those skilled in the art that as a result of the degeneracy of the genetic code, a multitude of GIPL-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring GIPL, and all such variations are to be considered as being specifically disclosed.

Although nucleotide sequences which encode GIPL and its variants are preferably capable of hybridizing to the nucleotide sequence of the naturally occurring gipl under appropriately selected conditions of stringency, it may be advantageous to produce nucleotide sequences encoding GIPL or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding GIPL and its derivatives without altering the encoded amino acid sequences include the production of RNA transcripts having more desirable properties, such as a greater half-life, than transcripts produced from the naturally occurring sequence.

The nucleotide sequences encoding GIPL may be joined to a variety of other nucleotide sequences by means of well established recombinant DNA techniques (cf Sambrook J et al. (1989) *Molecular Cloning: A Laboratory Manual*, Cold Spring Harbor Laboratory, Cold Spring Harbor N.Y.). Useful nucleotide sequences for joining to gipl include an assortment of cloning vectors, e.g., plasmids, cosraids, lambda phage derivatives, phagemids, and the like, that are well known in the art. Vectors of interest include expression vectors, replication vectors, probe generation vectors, and sequencing vectors. In general, vectors of interest will contain an origin of replication functional in at least one organism, convenient restriction endonuclease sensitive sites, and selectable markers for the host cell.

Another aspect of the subject invention is to provide for gipl specific nucleic acid hybridization probes capable of hybridizing with naturally occurring nucleotide sequences encoding GIPL. Such probes may also be used for the detection of related inhibitor encoding sequences and should preferably contain at least 50% of the nucleotides from any of these GIPL encoding sequences. The hybridization probes of the subject invention may be derived from the nucleotide sequence of the SEQ ID NOs: 1 and 5–12 or from genomic sequence including promoter, enhancer elements and introns of the naturally occurring gipl. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR as described U.S. Pat. Nos 4,683,195 and 4,965,188 provide additional uses for oligonucleotides based upon the nucleotide sequences which encode GIPL. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for gipl DNAs include the cloning of nucleic acid sequences encoding GIPL or GIPL derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding a GIPL and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a gipl sequence or any portion thereof.

The nucleotide sequences may be used to construct an assay to detect activation or induction of gipl due to inflammation or disease. The nucleotide sequence may be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with the sample, and the assay indicates the presence of the inducing inflammation and/or disease.

The nucleotide sequences for gipl may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a gipl on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

The nucleotide sequence encoding GIPL may be used to produce purified GIPL using well known methods of recombinant DNA technology. Among the many publications that teach methods for the expression of genes after they have been isolated is Goeddel (1990) Gene Expression Technology, Methods and Enzymology, Vol 185, Academic Press, San Diego. GIPL may be expressed in a variety of host cells, either prokaryotic or eukaryotic. Host cells may be from the same species from which a particular gipl nucleotide sequence was isolated or from a different species. Advantages of producing GIPL by recombinant DNA technology include obtaining adequate amounts of the protein for purification and the availability of simplified purification procedures.

Cells transformed with DNA encoding GIPL may be cultured under conditions suitable for the expression of GIPLs and recovery of the protein. GIPL produced by a recombinant cell may be secreted, contained intracellularly, or inserted into a membrane depending on the particular genetic construction used. In general, it is more convenient to prepare recombinant proteins in secreted form. Purification steps vary with the production process, the host organism and the particular protein produced.

In addition to recombinant production, fragments of GIPL may be produced by direct peptide synthesis using solid-phase techniques (cf Stewart et al (1969) Solid-Phase Peptide Synthesis, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of GIPL may be chemically synthesized separately and combined using chemical methods to produce the full length molecule.

GIPL for antibody induction does not require biological activity; however, the protein fragment, or oligopeptide must be immunogenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of GIPL amino acids may be fused with those of another protein such as keyhole limpet hemocyanin and antibody produced against the chimeric molecule.

Antibodies specific for GIPL may be produced by inoculation of an appropriate animal with the polypeptide or an antigenic fragment. An antibody is specific for the particular GIPL if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse W D et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding GIPL.

An additional embodiment of the subject invention is the use of GIPL specific antibodies, as bioactive agents to treat conditions associated with excessive phospholipase activity.

Bioactive compositions comprising agonists or antagonists of GIPL may be administered in a suitable therapeutic dose determined by any of several methodologies including clinical studies on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that a therapeutic, bioactive composition may be delivered by intravenous infusion into the bloodstream or any other effective means which could be used for treatment.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amine acid sequence as used herein refers to an oligopeptide, peptide, polypeptide or protein sequence.

"Peptide nucleic acid" as used herein refers to a molecule which comprises an oligomer to which an amine acid residue, such as lysine, and an amine group have been added. These small molecules, also designated anti-gene agents, stop transcript elongation by binding to their complementary (template) strand of nucleic acid (Nielsen P E et al (1993) Anticancer Drug Des 8:53–63).

As used herein, GIPL refers to the amine acid sequence of GIPL from any species, particularly mammalian, including bovine, ovine, porcine, murine, equine, and preferably human, in a naturally occurring form or from any source whether natural, synthetic, semi-synthetic or recombinant. As used herein, "naturally occurring" refers to an amine acid sequence which is found in nature.

The present invention also encompasses GIPL variants. A preferred GIPL variant is one having at least 80% amine acid sequence similarity, a more preferred GIPL variant is one having at least 90% amine acid sequence similarity and a most preferred GIPL variant is one having at least 95% amine acid sequence similarity to the GIPL amine acid sequence (SEQ ID NO: 2). A "variant" of GIPL may have an amine acid sequence that is different by one or more amine acid "substitutions". The variant may have "conservative"

changes, wherein a substituted amine acid has similar structural or chemical properties, eg, replacement of leucine with isoleucine. More rarely, a variant may have "nonconservative" changes, eg, replacement of a glycine with a tryptophan. Similar minor variations may also include amine acid deletions or insertions, or both. Guidance in determining which and how many amine acid residues may be substituted, inserted or deleted without abolishing biological or immunological activity may be found using computer programs well known in the art, for example, DNAStar software.

The term "biologically active" refers to a GIPL having structural, regulatory or biochemical functions of the naturally occurring GIPL. Likewise, "immunelogically active" defines the capability of the natural, recombinant or synthetic GIPL, or any oligopeptide thereof, to induce a specific immune response in appropriate animals or cells and to bind with specific antibodies.

The term "derivative" as used herein refers to the chemical modification of a gipl or the encoded GIPL. Illustrative of such modifications would be replacement of hydrogen by an alkyl, acyl, or amino group. A GIPL derivative would encode a polypeptide which retains essential biological characteristics of natural GIPL.

As used herein, the term "purified" refers to molecules, either nucleic or amino acid sequences, that are removed from their natural environment and isolated or separated from at least one other component with which they are naturally associated.

The GIPL Coding Sequences

The nucleic acid and deduced amino acid sequences of GIPL are shown in FIG. 1. In accordance with the invention, any nucleic acid sequence which encodes the amino acid sequence of GIPL can be used to generate recombinant molecules which express GIPL. In a specific embodiment described herein, the sequence for gipl was first isolated as Incyte Clone 156817 from a THP-1 cDNA library (THP1PBL02), patent application Ser. No. 08/438,571, entitled "Polynucleotides Derived from THP-1 Cells" by Delegeane et al. and filed May 10, 1995, the disclosure of which is incorporated herein by reference.

Methods for DNA sequencing are well known in the art and employ such enzymes as the Klenow fragment of DNA polymerase I, Sequenase® (US Biochemical Corp, Cleveland Ohio)), Taq polymerase (Perkin Elmer, Norwalk Conn.), thermostable T7 polymerass (Amersham, Chicago Ill.), or combinations of recombinant polymerases and proofreading exonucleases such as the ELONGASE Amplification System marketed by Gibco BRL (Gaithersburg Md.).

Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to sequences in public databases.

Extending the Polynucleotide Sequence

The polynucleotide sequence of gipl may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO®4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. Promoter-Finder™ a new kit available from Clontech (Palo Alto Calif.) uses PCR, nested primers and PromoterFinder libraries to walk in genomic DNA. This process avoids the need to screen libraries and is useful in finding intron/exon junctions.

Another PCR method, "Improved Method for Obtaining Full Length cDNA Sequences" by Guegler et al, patent application Ser. No. 08/487,112, filed Jun. 7, 1995 and hereby incorporated by reference, employs XL-PCR™ (Perkin Elmer) to amplify and extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode GIPL, fragments of the polypeptide, fusion proteins or functional equivalents thereof may be used to generate recombinant DNA molecules that direct the expression of GIPL in appropriate host cells. Due to the inherent degeneracy of the genetic code, other DNA sequences which encode substantially the same or a functionally equivalent amino acid sequence, may be used to clone and express GIPL. As will be understood by those of skill in the art, it may be advantageous to produce GIPL-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of GIPL expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of Figure I under various conditions of stringency. Hybridization conditions are based on the melting temperature (Tm) of the nucleic acid binding complex or probe, as taught in Berger and Kimmel (1987, *Guide to Molecular Cloning Techniques,* Methods in Enzymology, Vol 152, Academic Press, San Diego Calif.) incorporated herein by reference, and confer may be used at a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J (1994) *Dictionary of Biotechnology,* Stockton Press, New York N.Y.). Then by definition, hybridization includes the process of amplification as carried out in the polymerase chain reaction technologies described in Dieffenbach C W and G S Dveksler (1995, *PCR Primer, a Laboratory Manual,* Cold Spring Harbor Press, Plainview N.Y.) and incorporated herein by reference.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring gipl.

A "substitution" results from the replacement of one or more nucleotides or amino acids by different nucleotides or amino acids, respectively.

Altered gipl nucleic acid sequences which may be used in accordance with the invention include deletions, insertions or substitutions of different nucleotides resulting in a polynucleotide that encodes the same or a functionally equivalent GIPL. The protein may also show deletions, insertions or substitutions of amino acid residues which produce a silent change and result in a functionally equivalent GIPL. Deliberate amino acid substitutions may be made on the basis of similarity in polarity, charge, solubility, hydrophobicity, hydrophilicity, and/or the amphipathic nature of the residues as long as the biological activity of GIPL is retained. For example, negatively charged amino acids include aspartic acid and glutamic acid; positively charged amino acids include lysine and arginine; and amino acids with uncharged polar head groups having similar hydrophilicity values include leucine, isoleucine, valine; gtycine, alanine; asparagine, glutamine; serine, threonine phenylalanine, and tyrosine.

Included within the scope of the present invention are alleles of gipl. As used herein, an "allele" or "allelic sequence" is an alternative form of gipl. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The nucleotide sequences of the present invention can be engineered in order to alter a gipl coding sequence for a variety of reasons, including but not limited to, alterations which modify the cloning, processing and/or expression of the gens product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant gipl sequence may be ligated to a heterologous sequence to encode a fusion protein. For example, for screening of peptide libraries for inhibitors of GIPL activity, it may be useful to encode a chimeric GIPL protein that is recognized by a commercially available antibody. A fusion protein may also be engineered to contain a cleavage site located between a GIPL sequence and the heterologous protein sequence, so that the GIPL may be cleaved and purified away from the heterologous moiety.

In an alternate embodiment of the invention, the coding sequence of gipl could be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself could be produced using chemical methods to synthesize a GIPL amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer. The newly synthesized peptide can be purified by preparative high performance liquid chromatography (eg, Creighton (1983) *Proteins, Structures and Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of GIPL, or any part thereof, may be altered during direct synthesis and/or combined using chemical methods with sequences from other proteins, or any part thereof, to produce a variant polypeptide.

Expression Systems

In order to express a biologically active GIPL, the nucleotide sequence encoding GIPL or its functional equivalent, is inserted into an appropriate expression vector, ie, a vector which contains the necessary elements for the transcription and translation of the inserted coding sequence.

Methods which are well known to those skilled in the art can be used to construct expression vectors containing a GIPL coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual*, Cold Spring Harbor Press, Plainview N.Y. and Ausubel F M et al. (1989) *Current Protocols in Molecular Biology*, John Wiley & Sons, New York N.Y.

A variety of expression vector/host systems may be utilized to contain and express a gipl coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of gipl, vectors based on SV40 or EBV may be used with an appropriate selectable marker.

In bacterial systems, a number of expression vectors may be selected depending upon the use intended for GIPL. For example, when large quantities of GIPL are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the gipl coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding GIPL may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671:1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express gipl is an insect system. In one such system, *Autographa californica* nuclear polyhedrosis virus (AcNPV) is used as a vector to express foreign genes in *Spodoptera frugiperda* cells or in Trichoplusia larvae. The gipl coding sequence may be cloned into a nonessential region of the virus, such as the polyhedrin gene, and placed under control of the polyhedrin promoter. Successful insertion of gipl will render the polyhedrin gene inactive and produce recombinant virus lacking coat protein coat. The recombinant viruses are then used to infect *S. frugiperda* cells or Trichoplusia larvae in which GIPL is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a gipl coding sequence may be ligated into an adenovirus transcription/translation complex consisting of the late promoter and tripartite leader sequence. Insertion in a nonessential E1 or E3 region of the viral genome will result in a viable virus capable of expressing GIPL in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a gipl sequence. These signals include the ATG initiation codon and adjacent sequences. In cases where gipl, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express gipl may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the gipl is inserted within a marker gene sequence, recombinant cells containing gipl can be identified by the absence of marker gene function. Alternatively, a marker gene can be placed in tandem with a GIPL sequence under the control of a single promoter. Expression of the marker gene in response to induction or selection usually indicates expression of the tandem gipl as well.

Alternatively, host cells which contain the coding sequence for gipl and express GIPL may be identified by a variety of procedures known to those of skill in the art. These procedures include, but are not limited to, DNA—DNA or DNA-RNA hybridization and protein bioassay or immunoassay techniques which include membrane, solution, or chip based technologies for the detection and/or quantification of the nucleic acid or protein.

The presence of the gipl polynucleotide sequence can be detected by DNA—DNA or DNA-RNA hybridization or amplification using probes, portions or fragments of gipl. Nucleic acid amplification based assays involve the use of oligonucleotides or oligomers based on the gipl sequence to detect transformants containing gipl DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of GIPL, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on GIPL is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to gipl include oligolabeling, nick translation, end-labeling or PCR amplification using a labeled nucleotide. Alternatively, the gipl sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of GIPL

Host cells transformed with a gipl nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing gipl can be designed with signal sequences which direct secretion of GIPL through a prokaryotic or eukaryotic cell membrane. Other recombinant constructions may join gipl to nucleotide sequence encoding a polypeptide domain which will facilitate purification of soluble proteins (Kroll D J et al (1993) DNA Cell Biol 12:441–53; cf discussion of vectors infra containing fusion proteins).

GIPL may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and GIPL is useful to facilitate purification.

Uses of GIPL

Figure 5:
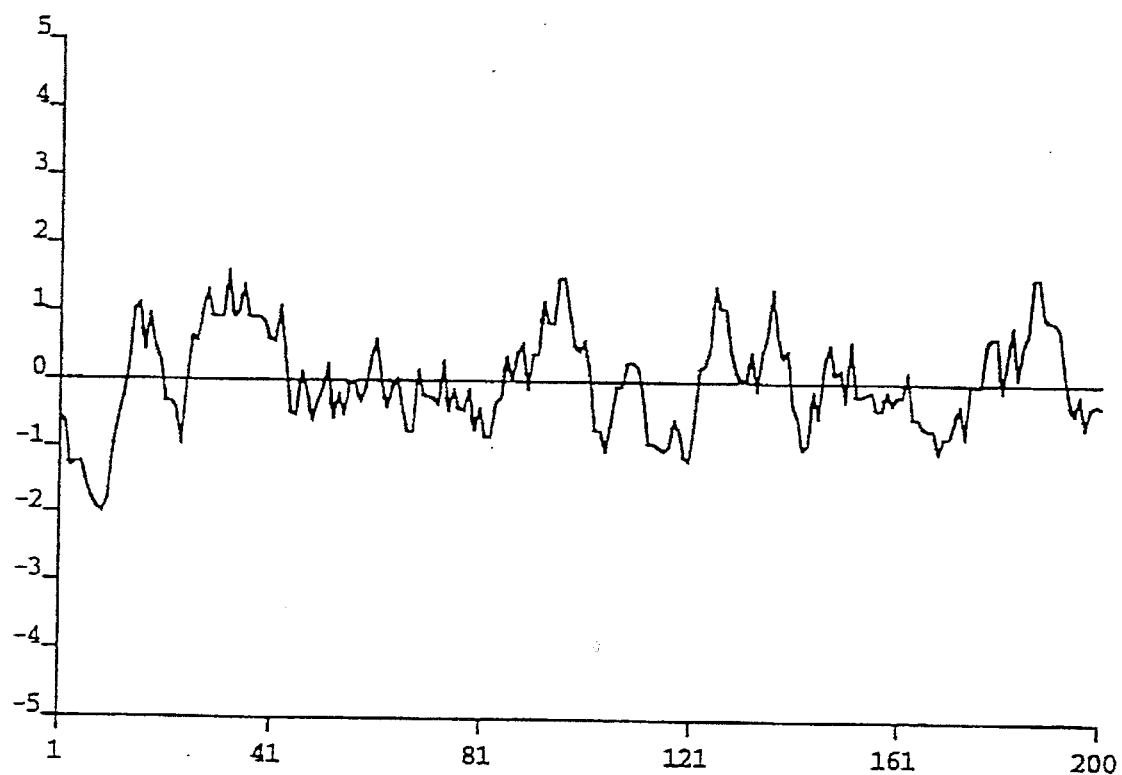
FIG. 5 shows the hydrophobicity plot for CNF. The X axis reflects amino acid position, and the negative Y axis, hydrophobicity. The hydrophobicity plot was generated using MacDNAsis software.
Figure 6:
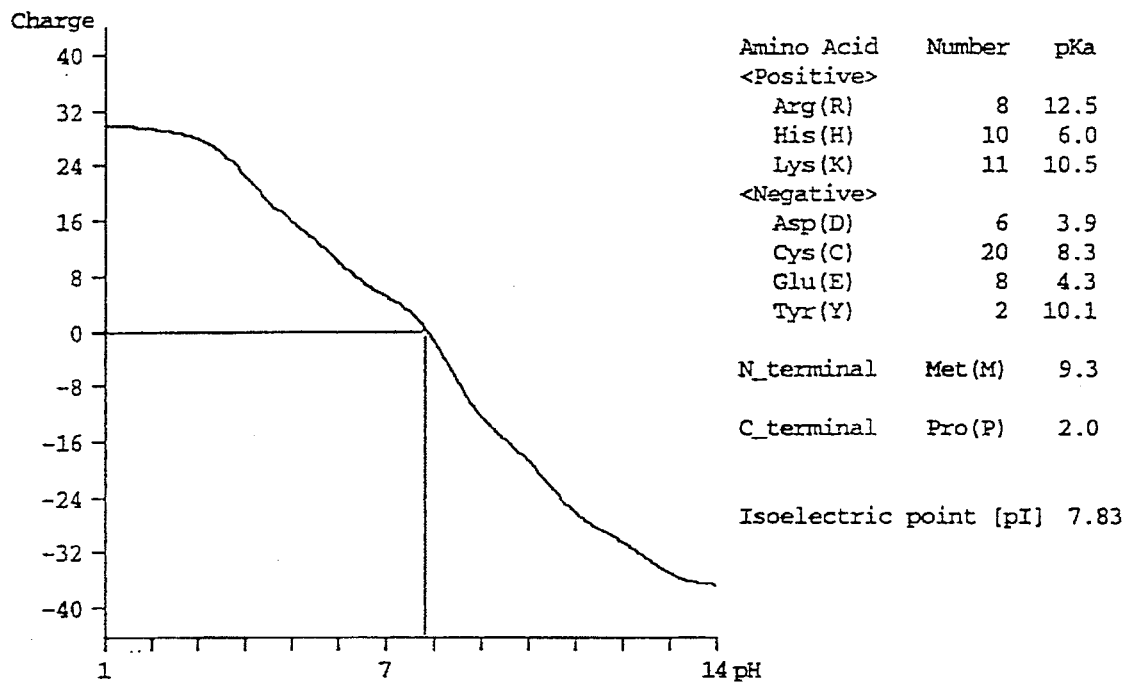
FIG. 6 shows the isolelectric plot for GIPL. This plot was generated using MacDNAsis software.
Figure 7:
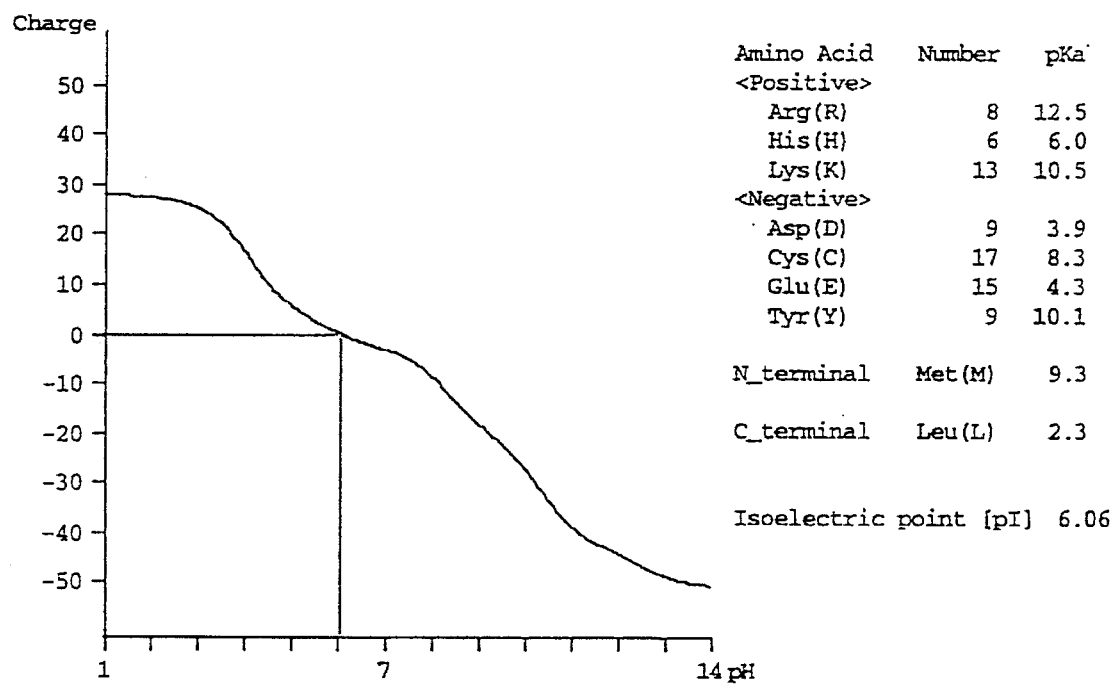
FIG. 7 shows the isolelectric plot for CNF. This plot was generated using MacDNAsis software.

The rationale for diagnostic and therapeutic uses of the nucleotide and peptide sequences disclosed herein is based on the disclosed nucleic acid and amino acid sequences, the information from comparisons between GIPL and CNF as shown in FIGS. 3–7, and the presence of the gipl transcript in the mast cell (HMC1NOT1), THP-1, neuronal (PGANNOT01) and uterus (UTRSNOT01) cDNA libraries. It must be noted that these libraries were made from activated cells or the cells or tissues removed from patients or victims of accidental death.

The nucleic acid sequence (SEQ ID NO: 1), its complement, fragments or oligomers, and anti-GIPL antibodies may be used as diagnostic compositions to assay bodily fluids or extracts of biological samples for expression of gipl. Purified polynucleotides and polypeptides can be used as positive controls in their respective nucleic acid or protein based assays to validate and quantitate the expression of gipl either during preliminary diagnosis or during the course of therapeutic treatment for a particular condition or disease. In some cases, the mere presence of gipl or GIPL (expression vs. absence of expression) will connote disease, while in other cases, gipl expression will be abnormal because gipl or GIPL deviates from a predetermined normal level.

Some of the conditions in which the moderation of phospholipase expression may be important include viral, bacterial or fungal infections including septic and toxic shock and gangrene; autoimmune responses encompassing but not limited to anemias, asthma, systemic lupus, and myasthenia gravis; hereditary or cancerous conditions such as Alzheimer's, breast carcinoma, diabetes mellitus, osteoporosis, and schizophrenia; glomerulonephritis; pregnancy; rheumatoid and osteoarthritis; scleroderma; and insect or snake bites or stings in which phospholipases are a component of the injected venom.

The use of GIPL, and of the nucleic acid sequences which encode it, is based on the amino acid sequence and structural homology based on cysteine distribution between GIPL and CNF. The timing of and amount of expression of phospholipases and GIPL are implicated in the conditions previously recited. In each of the next three situations, the level of phospholipase expression precedes or exceeds the expression of GIPL.

Phospholipases play a role in membrane turnover in normal as well as cancerous tissues. Supplying purified GIPL to the cancerous tissues would interfere with metastasis and growth of neoplastic cells. Similarly, supplying purified GIPL to individuals with developing tumors would interfere with anglogenesis, the vascularization of the tumor which supports prolific growth.

In reproductive studies, Reponen P et al. (1995; Dev Dyn 202:388–96) has discussed the enzymes which are active in remodeling during implantation of the embryo. The phospholipases are involved in membrane reconstruction during this process. Therefore, the timely inhibition of these phospholipases, post coitus, by supplying women with recombinant GIPL would inhibit the membrane remodeling process, in effect, preventing implantation and pregnancy.

In diseases such as osteoarthritis, rheumatoid arthritis, pulmonary emphysema, periodontal disease, systemic lupus, and osteoporosis or with infectious conditions such as septic or toxic shock or gangrene, the excess activity of the phospholipases producing arachidonic acid or diacylglycerol and contributing to the formation or eicosanoids causes inflammation, tissue destruction, impaired function or death. Appropriate delivery of GIPL would inhibit the activity of the phospholipases and their continued induction by eicosanoids (such as the LKB4) significantly reducing inflammation and damage. Similarly, the delivery of a GIPL-specific agonist would prolong the effects of GIPL.

Purified GIPL may also be administered as an antivenom in those cases of snake or insect bite where phospholipases are an active component of the venom. Supplying a pharmaceutical composition containing GIPL inactivates the neurotoxic, cardiotoxic, myotoxic, anticoagulent and platelet-activating activities of venom.

GIPL Antibodies

Procedures well known in the art can be used for the production of antibodies to GIPL. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc. may be immunized by injection with GIPL or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol.

BCG (bacilli Calmette-Guerin) and *Corynebacterium parvum* are potentially useful human adjuvants.

Monoclonal antibodies to GIPL may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452-454). Alternatively, techniques described for the production of single chain antibodies (U.S. Pat. No. 4,946,778) can be adapted to produce GIPL-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86:3833–3837), and Winter G and Milstein C (1991; Nature 349:293–299).

Antibody fragments which contain specific binding sites for GIPL may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275–1281).

GIPL-specific antibodies are useful for the diagnosis of conditions and diseases associated with expression of GIPL. A variety of protocols for competitive binding or immunoradiometric assays using either polyclonal or monoclonal antibodies with established specificities are well known in the art. Such immunoassays typically involve the formation of complexes between GIPL and its specific antibody and the measurement of complex formation. A two-site, monoclonal-based immunoassay utilizing monoclonal antibodies reactive to two noninterfering epitopes on a specific GIPL protein is preferred, but a competitive binding assay may also be employed. These assays are described in Maddox D E et al (1983, J Exp Med 158:1211).

Diagnostic Assays Using GIPL Specific Antibodies

Particular GIPL antibodies are useful for the diagnosis of conditions or diseases characterized by expression of GIPL or in assays to monitor patients being treated with GIPL, agonists or inhibitors. Diagnostic assays for GIPL include methods utilizing the antibody and a label to detect GIPL in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring GIPL, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on GIPL is preferred, but a competitive binding assay may be employed. These assays are described, among other places, in Maddox, D E et al (1983, J Exp Med 158:1211).

In order to provide a basis for diagnosis, normal or standard values for GIPL expression must be established. This is accomplished by combining body fluids or cell extracts taken from normal subjects, either animal or human, with antibody to GIPL under conditions suitable for complex formation which are well known in the art. The amount of standard complex formation may be quantified by comparing various artificial membranes containing known quantities of GIPL with both control and disease samples from biopsied tissues. Then, standard values obtained from normal samples may be compared with values obtained from samples from subjects potentially affected by disease. Deviation between standard and subject values establishes the presence of disease state.

Drug Screening

GIPL, its catalytic or immunogenic fragments or oligopeptides, can be used for screening therapeutic compounds in any of a variety of drug screening techniques. The fragment employed in such a test may be free in solution, affixed to a solid support, borne on a cell surface, or located intracellularly. The formation of binding complexes, between GIPL and the agent being tested, may be measured.

Another technique for drug screening which provides for high throughput screening of compounds having suitable binding affinity to the GIPL is described in detail in "Determination of Amino Acid Sequence Antigenicity" by Geysen H N, WO application Ser. No. 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of GIPL and washed. Bound GIPL is then detected by methods well known in the art. Purified GIPL can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding GIPL specifically compete with a test compound for binding GIPL. In this manner, the antibodies can be used to detect the presence of any peptide which shares one or more antigenic determinants with GIPL.

Uses of the Polynucleotide Encoding GIPL

A polynucleotide, gipl, or any part thereof, may be used for diagnostic and/or therapeutic purposes. For diagnostic purposes, the gipl of this invention may be used to detect and quantitate gene expression in biopsied tissues in which expression of GIPL may be implicated. The diagnostic assay is useful to distinguish between absence, presence, and excess expression of gipl and to monitor regulation of gipl levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding GIPL or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring gipl, alleles or related sequences.

Diagnostics

Polynucleotide sequences encoding GIPL may be used for the diagnosis of conditions or diseases with which the expression of GIPL is associated. For example, polynucleotide sequences encoding GIPL may be used in hybridization or PCR assays of fluids or tissues from biopsies to detect gipl expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for gipl expression must be established. This is accomplished by combining body fluids or cell extracts taken from normal subjects, either animal or human, with gipl, or a portion thereof, under conditions suitable for hybridization or amplification. Standard hybridization may be quantified by comparing the values obtained for normal subjects with a dilution series of gipl run in the same experiment where a known amount of purified gipl is used. Standard values obtained from normal samples may be compared with values obtained from samples from patients affected by gipl-associated diseases. Deviation between standard and subject values establishes the presence of disease.

Once disease is established, a therapeutic agent is administered; and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the gipl sequence. Such oligomers are generally chemically synthesized, but they may be generated enzymatically or produced from a recombinant source. Oligomers generally comprise two nucleotide sequences, one with sense orientation (5'->3') and one with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of gipl in extracts of biopsied tissues may indicate the onset of cancer. A definitive diagnosis of this type may allow health professionals to begin aggressive treatment and prevent further worsening of the condition. Similarly, further assays can be used to monitor the progress of a patient during treatment.

Therapeutics

The polynucleotide disclosed herein may be useful in the treatment of various inherited conditions such as autoimmune, hereditary and cancerous conditions, pregnancy, and infections or bites and stings resulting in shock or anaphylaxis. For example, administration of a vector containing and expressing gipl provides a means to moderate the phospholipase activity which leads to rapid membrane remodeling in schizophrenia. By introducing the antisense molecules (anti-gipl) into the cerebrospinal fluid, gene therapy via expression of GIPL can be used to reduce or eliminate phospholipase activity.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antigipl. See, for example, the techniques described in Maniatis et al (supra) and Ausubel et al (supra).

The polynucleotides comprising full length cDNA sequence and/or its regulatory elements enable researchers to use gipl as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding GIPL can be turned off by transfecting a cell or tissue with expression vectors which express high levels of the desired fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettier I, personal communication) and even longer if appropriate replication elements are part of the vector system.

As mentioned above, modifications of gene expression can be obtained by designing antisense molecules, DNA, RNA or PNA, to the control regions of gipl, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al. (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of gipl.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in Vitro and in Viv0 transcription of DNA sequences encoding GIPL. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented as U.S. Pat. Nos. 5,399,493 and 5,437,994, disclosed herein by reference. Delivery by transfection and by liposome are quite well known in the art.

Furthermore, the nucleotide sequences for gipl disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for gipl can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al. (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention comprises pharmaceutical compositions which may comprise nucleotides, proteins, antibodies, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally, Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Penna.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penerrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of GIPL, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors.

Similarly, delivery of polynucleotides or polypeptides will be specific to particular cells, conditions, locations, etc.

It is contemplated, for example, that GIPL can be delivered in a suitable formulation to block the accelerated turnover of membranes associated with phospholipase activity in schizophrenia (Gattaz W F et al. (1995) Schizophr Res 16:1–6). In a clinical setting, the monitoring of the patient's mental and emotional condition as well as arachidonic acid, diacylglycerol, or eicosanoid levels will allow the attending physician to adjust dosage of the pharmaceutical composition. Similarly, administration of identified agonists should accelerate or extend native GIPL activity accomplishing a similar amelioration of the disease state.

The examples below are provided to illustrate the subject invention and are not included for the purpose of limiting the invention.

EXAMPLES

I THP1PLB02 cDNA Library Construction

THP-1 is a human leukemic cell line with distinct monocytic characteristics. This cell line was derived from the blood of a 1-year-old boy with acute monocytic leukemia (Tsuchiya S et al (1980) Int J Cancer 26:171–176). Cells were cultured for 48 hr with 100 nm phorbol in DMSO and for 4 hr with 1 µg/ml LPS. The PMA+LPS-stimulated cells represent activated macrophages. The cDNA libraries was custom constructed by Stratagene (La Jolla Calif.) essentially as described below.

Stratagene prepared the cDNA library using oligo d(T) priming. Synthetic adapter oligonucleotides were ligated onto the cDNA molecules enabling them to be inserted into the Uni-ZAP™ vector system (Stratagene). The quality of the cDNA library was screened using DNA probes, and then, the pBluescript® phagemid (Stratagene) was excised. The library phage particles were infected into E. coil host strain XL1-Blue® (Stratagene). Alternative unidirectional vectors include, but are not limited to, pcDNAI (Invitrogen, San Diego Calif.) and pSHlox-1 (Novagen, Madison Wis.).

II Isolation of cDNA Clones

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBiuescript phagemid and the cDNA insert. The phagemid DNA was released from the cells, purified, and used to reinfect fresh SOLR™ host cells (Stratagene) The newly transformed bacteria were selected on medium containing ampicillin and produced double-stranded phagemid DNA.

An alternate method for purifying phagemid utilizes the Miniprep Kit (Catalog No. 77468, available from Advanced Genetic Technologies Corporation, Gaithersburg Md.). This kit has a 96-well format and provides reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 µl of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

Phagemid DNA may also be purified using the QIAWELL-8 Plasmid Purification System from QIAGEN Inc (Chatsworth Calif.). This high throughput method provides lysis of the bacterial cells and isolation of highly purified phagemid DNA using QIAGEN® anion-exchange resin particles with EMPORE™ membrane technology (3M, Minneapolis Minn.) in a multiwell format. The DNA was eluted from the purification resin and prepared for DNA sequencing and other analytical manipulations.

The cDNAs were sequenced by the method of Sanger F and A R Coulson (1975; J Mol Biol 94:441f), using a either Applied Biosystems Catalyst 800 or a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems; and the reading frame was determined.

III Homology Searching of cDNA Clones and their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Extension of GIPL to Full Length or to Recover Regulatory Elements

The nucleic acid sequence of full length GIPL (SEQ ID NO: 1) may be used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known GIPL sequence "outward" generating amplicons containing new, unknown nucleotide sequence for the region of interest. The initial primers may be designed from the cDNA using OLIGO® 4.06 Primer Analysis Software (National Biosciences), or another appropriate program, to be 22–30 nucleotides in length, to have a GC content of 50% or more, and to anneal to the target sequence, at temperatures about 68°–72° C. Any stretch of nucleotides which would result in hairpin structures and primer-primer dimerizations is avoided.

The original cDNA library may be used to extend the sequence or a human genomic library is used to extend and amplify 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO: 1 may be employed to screen cDNAs, genomic DNAs or mRNAs. Although the labeling of oligonucleotides, consisting of about 20 base-pairs, is specifically described, essentially the same procedure may be used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The gipl sequence, or any part thereof, may be used to inhibit in vivo or in vitro expression of native gipl. Although use of antisense oligonucleotides, comprising about 20 base-pairs, is specifically described, essentially the same procedure may be used with larger cDNA fragments. An oligonucleotide based on the coding sequence of GIPL as shown in FIG. 1 may be used to inhibit expression of native GIPL. The complementary oligonucleotide can be designed from the most unique 5' sequence as shown in FIG. 2 and used either to inhibit transcription by preventing promoter binding to the upstream nontranslated sequence or translation of a gipl transcript by preventing the ribosome from binding. Using an appropriate portion of the leader and 5' sequence of SEQ ID NO: 1, an effective antisense oligonucleotide would include approximately 66 codons spanning the region which translates into the first 22 residues of the signal and coding sequence of the polypeptide as shown in FIG. 1.

VII Expression of GIPL

Expression of the GIPL may be accomplished by subcloning the cDNAs into appropriate vectors and transfecting the vectors into host cells. In this case, the cloning vector, pSport, previously used for the generation of the cDNA library is used to express GIPL in *E. coil*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length GIPL. The signal sequence directs the secretion of GIPL into the bacterial growth media which can be used directly in the following assay for activity.

VIII GIPL Activity

An erthrocyte membrane assay may be used to quantitate GIPL activity. Erthrocytes and various phospholipases are placed in eppendorf tubes in appropriate media and under appropriate conditions for the digestion of membrane phospholipids. After approximately one hour, samples are removed and analyzed for arachidonic acid and diacyglycerol using high performance liquid chromatography (HPLC). The HPLC results represent the control set against which a GIPL-containing experimental set is compared. In the experimental set, erythrocytes are incubated with phospholipases and GIPL. The effective inhibition of the phospholipases by the GIPL molecule disclosed herein is reflected in a lower amount of (or lack of) arachidonic acid or diacylglycerol in the media from the experimental tubes.

IX Production of GIPL Specific Antibodies

Although GIPL purified using PAGE electrophoresis (Maniatis, supra) can be used to immunize rabbits using standard protocols, a monoclonal approach is more commonly employed. The amino acid sequence translated from GIPL is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F M et al (supra) and shown in FIG. 4.

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X Purification of Native GIPL Using Specific Antibodies

Native or recombinant GIPL can be purified by immunoaffinity chromatography using antibodies specific for GIPL. An immunoaffinity column is constructed by covalently coupling GIPL antibody to an activated chromatographic resin such as CnBr-activated Sepharose (Pharmacia Biotech). After the coupling, the resin is blocked and washed according to the manufacturer's instructions.

Media containing GIPL is passed over the immunoaffinity column, and the column is washed under conditions that allow the preferential absorbance of GIPL (eg, high ionic strength buffers in the presence of detergent). The column is eluted under conditions that disrupt antibody/GIPL binding (eg, a buffer of pH 2-3 or a high concentration of a chaotrope such as urea or thiocyanate ion), and GIPL is collected.

XI Identification of Molecules Which Interact with GIPL

GIPL, or biologically active fragments thereof, are labelled with $^{125}$I Bolton-Hunter reagent (Bolton, A E and Hunter, W M (1973) Biochem J 133:529). Candidate molecules previously arrayed in the wells of a 96 well plate are incubated with the labelled GIPL, washed and any wells with labelled GIPL complex are assayed. Data obtained using different concentrations of GIPL are used to calculate values for the number, affinity, and association of GIPL with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A purified polynucleotide encoding a polypeptide with an amino acid sequence shown in SEQ ID NO: 2.

2. The polynucleotide of claim 1 wherein the nucleic acid sequence consists of SEQ ID NO: 1, or its complement.

3. An expression vector comprising the polynucleotide of claim 1.

4. A host cell transformed with the expression vector of claim 3.

5. A method for producing a polypeptide consisting of the amino acid sequence shown in SEQ ID NO: 2, the method comprising the steps of:

a) culturing the host cell of claim 4 to allow expression of the polypeptide; and b) recovering the polypeptide from the host cell culture.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 839 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1LPB02
        ( B ) CLONE: CONSENSUS ( x i ) SEQUENCE DESCRIPTION: SEQ ID NO:1:

```
NCAATGGGCC  GGCCGTGGGA  AGGGTGAATG  TGGGTCCAGA  CCCGCCCCTC  CTCAGCTTCC     60
TATAAAAGCT  GGGGACCAGG  TACTGCTGAT  ACACACACCA  TGAGGCTCTC  CAGGAGACCA    120
GAGACCTTTC  TGCTGGCCTT  TGTGTTGCTC  TGCACCCTCC  TGGGTCTTGG  GTGCCCACTA    180
CACTGCGAAA  TATGTACGGC  GGCGGGGAGC  AGGTGCCATG  GCCAAATGAA  GACCTGCAGC    240
AGTGACAAGG  ACACATGTGT  GCTCCTGGTC  GGGAAGGCTA  CTTCAAAGGG  CAAGGAGTTG    300
GTGCACACCT  ACAAGGGCTG  CATCAGGTCC  CAGGACTGCT  ACTCCGGCGT  TATATCCACC    360
ACCATGGGCC  CCAAGGACCA  CATGGTAACC  AGCTCCTTCT  GCTGCCAGAG  CGACGGCTGC    420
AACAGTGCCT  TTTTGTCTGT  TCCCTTGACC  AATCTTACTG  AGAATGGCCT  GATGTGCCCC    480
GCCTGCACTG  CGAGCTTCAG  GGACAAATGC  ATGGGGCCCA  TGACCCACTG  TACTGGAAAG    540
GAAAACCACT  GCGTCTCCTT  ATCTGGACAC  GTGCAGGCTG  GTATTTTCAA  ACCCAGATTT    600
GCTATGCGGG  GCTGTGCTAC  AGAGAGTATG  TGCTTTACCA  AGCCTGGTGC  TGAAGTACCC    660
ACAGGCACCA  ATGTCCTCTT  CCTCCATCAT  ATAGAGTGCA  CTCACTCCCC  CTGAAAAGCT    720
ATCTGAACAG  AGGAAGATAA  TGTAGTGTGA  AGTCCCCATT  TGTCCTCAGC  CTGTAACTTC    780
CCCGTGTGCC  TATAAAGAAG  TTAATAGAGC  AAAAAAAAAA  AAAAAAAAA   AAACTCGAG     839
```

( 2 ) INFORMATION FOR SEQ ID NO:2:

( i ) SEQUENCE CHARACTERISTICS:
        ( A ) LENGTH: 204 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: THP1LPB02
        ( B ) CLONE: CONSENSUS ( x i ) SEQUENCE DESCRIPTION: SEQ ID NO:2:

```
Met  Arg  Leu  Ser  Arg  Arg  Pro  Glu  Thr  Phe  Leu  Leu  Ala  Phe  Val  Leu
 1             5                   10                          15

Leu  Cys  Thr  Leu  Leu  Gly  Leu  Gly  Cys  Pro  Leu  His  Cys  Glu  Ile  Cys
              20                  25                          30

Thr  Ala  Ala  Gly  Ser  Arg  Cys  His  Gly  Gln  Met  Lys  Thr  Cys  Ser  Ser
              35                  40                  45

Asp  Lys  Asp  Thr  Cys  Val  Leu  Leu  Val  Gly  Lys  Ala  Thr  Ser  Lys  Gly
         50                  55                  60
```

| Lys<br>65 | Glu | Leu | Val | His | Thr<br>70 | Tyr | Lys | Gly | Cys<br>75 | Ile | Arg | Ser | Gln | Asp<br>80 | Cys |
|---|---|---|---|---|---|---|---|---|---|---|---|---|---|---|---|
| Tyr | Ser | Gly | Val | Ile<br>85 | Ser | Thr | Thr | Met | Gly<br>90 | Pro | Lys | Asp | His | Met<br>95 | Val |
| Thr | Ser | Ser | Phe<br>100 | Cys | Cys | Gln | Ser | Asp<br>105 | Gly | Cys | Asn | Ser | Ala<br>110 | Phe | Leu |
| Ser | Val | Pro<br>115 | Leu | Thr | Asn | Leu | Thr<br>120 | Glu | Asn | Gly | Leu | Met<br>125 | Cys | Pro | Ala |
| Cys | Thr<br>130 | Ala | Ser | Phe | Arg | Asp<br>135 | Lys | Cys | Met | Gly | Pro<br>140 | Met | Thr | His | Cys |
| Thr<br>145 | Gly | Lys | Glu | Asn | His<br>150 | Cys | Val | Ser | Leu | Ser<br>155 | Gly | His | Val | Gln | Ala<br>160 |
| Gly | Ile | Phe | Lys | Pro<br>165 | Arg | Phe | Ala | Met | Arg<br>170 | Gly | Cys | Ala | Thr | Glu<br>175 | Ser |
| Met | Cys | Phe | Thr<br>180 | Lys | Pro | Gly | Ala | Glu<br>185 | Val | Pro | Thr | Gly | Thr<br>190 | Asn | Val |
| Leu | Phe | Leu<br>195 | His | His | Ile | Glu | Cys<br>200 | Thr | His | Ser | Pro | | | | |

(2) INFORMATION FOR SEQ ID NO:3:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: GI 501050

(xi) SEQUENCE DESCRIPTION: SEQ ID NO:3:

| Met<br>1 | Lys | Tyr | Leu | His<br>5 | Thr | Ile | Cys | Leu | Leu<br>10 | Phe | Ile | Phe | Val | Ala<br>15 | Arg |
|---|---|---|---|---|---|---|---|---|---|---|---|---|---|---|---|
| Gly | Asn | Ser | Arg<br>20 | Ser | Cys | Asp | Phe | Cys<br>25 | His | Asn | Ile | Gly | Lys<br>30 | Asp | Cys |
| Asp | Gly | Tyr<br>35 | Glu | Glu | Glu | Cys | Ser<br>40 | Ser | Pro | Glu | Asp | Val<br>45 | Cys | Gly | Lys |
| Val | Leu<br>50 | Leu | Glu | Ile | Ser | Ser<br>55 | Ala | Ser | Leu | Ser | Val<br>60 | Arg | Thr | Val | His |
| Lys<br>65 | Asn | Cys | Phe | Ser | Ser<br>70 | Ser | Ile | Cys | Lys | Leu<br>75 | Gly | Gln | Phe | Asp | Val<br>80 |
| Asn | Ile | Gly | His | His<br>85 | Ser | Tyr | Ile | Arg | Gly<br>90 | Arg | Ile | Asn | Cys | Cys<br>95 | Glu |
| Lys | Glu | Leu | Cys<br>100 | Glu | Asp | Gln | Pro | Phe<br>105 | Pro | Gly | Leu | Pro | Leu<br>110 | Ser | Lys |
| Pro | Asn | Gly<br>115 | Tyr | Tyr | Cys | Pro | Gly<br>120 | Ala | Ile | Gly | Leu | Phe<br>125 | Thr | Lys | Asp |
| Ser | Thr<br>130 | Glu | Tyr | Glu | Ala | Ile<br>135 | Cys | Lys | Gly | Thr | Glu<br>140 | Thr | Lys | Cys | Ile |
| Asn<br>145 | Ile | Val | Gly | His | Arg<br>150 | Tyr | Glu | Gln | Phe | Pro<br>155 | Gly | Asp | Ile | Ser | Tyr<br>160 |
| Asn | Leu | Lys | Gly | Cys<br>165 | Val | Ser | Ser | Cys | Pro<br>170 | Leu | Leu | Ser | Leu | Ser<br>175 | Asn |
| Ala | Thr | Phe | Glu<br>180 | Gln | Asn | Arg | Asn | Tyr<br>185 | Leu | Glu | Lys | Val | Glu<br>190 | Cys | Lys |

Asp Ala Ile Arg Leu Ala Ser Leu
      195                 200

( 2 ) INFORMATION FOR SEQ ID NO:4:

( i ) SEQUENCE CHARACTERISTICS:
        ( A ) LENGTH: 327 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: HMC1N0T01
        ( B ) CLONE: 8941

( x i ) SEQUENCE DESCRIPTION: SEQ ID NO:4:

| | | | | | | |
|---|---|---|---|---|---|---|
| GGAGGCCTAG | GGTTAGGCAA | GACCTTGAGG | CAGGGGTTGA | AGCCAGGGAG | TGGTCAGCCA | 60 |
| GCACTGTCCC | TGCCTGTCCC | CATCCACAG | AGGGCAAGGA | GTTGGTGCAC | ACCTACAAGG | 120 |
| GCTGCATCAG | GTCCAGGAC | TGCTACTCCG | GCGTTATATC | NACCACCATG | GGCCCCAAGG | 180 |
| ACCACATGGT | AACCAGCTCC | TTCTGNTGCC | AGAGCGACGG | CTGCAACAGT | GCCTTTTGT | 240 |
| CTGTTCCCTT | GACCAATCTT | ACTGAGAATG | GCCTGATGTG | CCCNGCTGCA | CTGCGAGTTT | 300 |
| NAGGGNCAAA | ATNCATGGGG | GCCCATT | | | | 327 |

( 2 ) INFORMATION FOR SEQ ID NO:5:

( i ) SEQUENCE CHARACTERISTICS:
        ( A ) LENGTH: 324 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1LPB01
        ( B ) CLONE: 10033

( x i ) SEQUENCE DESCRIPTION: SEQ ID NO:5:

| | | | | | | |
|---|---|---|---|---|---|---|
| GTTGCTCTNC | ACCCTCCTGG | GTCTTGGGTG | CCCACTACAC | TGCGAAATAT | GTACGGCGGC | 60 |
| GGGGAGCAGG | TGCCATGGCC | AAATGAAGAC | CTGCAGCAGT | GACAAGGACA | CATGTGTGCT | 120 |
| CCTGGTCGGG | AAGGCTACTT | CAAAGGGCAA | GGAGTTGGTG | CACACCTACA | AGGGCTGCAT | 180 |
| CAGGTCCCAG | GACTGCTACT | CCGGCGTTAT | ATCCACCACC | ATGGGCCCCA | AGGACCACAT | 240 |
| GGTAACCAGC | TCCTTCTGCT | GCAGAGCGAC | GGCTGCAACA | GTGCCTTTTT | GTCTGTTCCC | 300 |
| TTGACCAATC | TTACTGAGAA | TGGT | | | | 324 |

( 2 ) INFORMATION FOR SEQ ID NO:6:

( i ) SEQUENCE CHARACTERISTICS:
        ( A ) LENGTH: 262 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1LPB01
        ( B ) CLONE: 10644

( x i ) SEQUENCE DESCRIPTION: SEQ ID NO:6:

| | | | | | | |
|---|---|---|---|---|---|---|
| GACACATGTG | TNCTCCTGGT | CGGGAAGGCT | ACTTCAAAGG | GCAAGGAGTT | GGTGCACACC | 60 |

```
TACAAGGGCT GCATCAGGTN CCAGGACTGC TACTCCGGNG TTATATCCAC CACCATGGGC      120

CCCAAGGACC ACATGGTAAC CAGCTCCTTC TGCTGCCAGA GCGACGGCTG CAACAGTGCC      180

TTTTTGTCTG TTCCCTTGAC CAATNTTACT GAGAATNGNC TGATGTGCCC CGNCTGCACT      240

GNGAGCTTCA GGGACAAATG CT                                               262
```

( 2 ) INFORMATION FOR SEQ ID NO:7:

( i ) SEQUENCE CHARACTERISTICS:
        ( A ) LENGTH: 310 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1LPB01
        ( B ) CLONE: 10774

( x i ) SEQUENCE DESCRIPTION: SEQ ID NO:7:

```
GACACATGTG TGCTCCTGGT CGGGAAGGCT ACTTCAAAGG GCAAGGAGTT GGTGCACACC      60

TACAAGGGCT GCATCAGGTC CCAGGACTGC TACTCCGGNG TTATATCCAC CACCATGGGC      120

CCCAAGGACC ACATGGTAAC CAGCTCCTTC TGCTGCCAGA GCGACGGCTG CAACAGTGCC      180

TTTTTGTCTG TTCCCTTANC CAATCTTACT GAGAATGGCC TGATGTGCCC CGNCTGAACT      240

NCGAGCTTCA GGGACAAATN CATGGGNCNA TGACCCACTG TACTGGNAAG NNAAACCACT      300

GNGTGTCCTT                                                             310
```

( 2 ) INFORMATION FOR SEQ ID NO:8:

( i ) SEQUENCE CHARACTERISTICS:
        ( A ) LENGTH: 185 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1PEB01
        ( B ) CLONE: 71854

( x i ) SEQUENCE DESCRIPTION: SEQ ID NO:8:

```
CTCCGGCGTT ATATCCACCA CCATGGGCCC CAAGGACCAC ATGGTAACCA GCTCCTTCTG      60

CTGCCAGAGC GACGGCTGCA ACANTGCCTT TTTNTNTGTT CCCTTGACCA ATCTTACTGA      120

GAATGGCCTG ATGTGCCCCG CCTGCACTGC GAGCTTCAGG GACAAATGCA TGGGGCCCAT      180

GACCC                                                                  185
```

( 2 ) INFORMATION FOR SEQ ID NO:9:

( i ) SEQUENCE CHARACTERISTICS:
        ( A ) LENGTH: 151 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1PEB01
        ( B ) CLONE: 72861

( x i ) SEQUENCE DESCRIPTION: SEQ ID NO:9:

```
TTTGGTGCAC ACCTACAAGG GCTGCATCAG GTCCCAGGAC TTCTACTCCG GNGTTATATC    60

CACCACCATG GGCCCCAAGG ACCACATGGT AACCAGCTCC TTNTGCTGCC AGAGCGACGG    120

CTGCAACATT GCCTTTTTNT NTGTNCCCTT G                                  151
```

( 2 ) INFORMATION FOR SEQ ID NO:10:

( i ) SEQUENCE CHARACTERISTICS:
        ( A ) LENGTH: 144 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1PEB01
        ( B ) CLONE: 74452

( x i ) SEQUENCE DESCRIPTION: SEQ ID NO:10:

```
CAGGACTGCT ACTCCGGNGT TATATCCACC ACCATGGGCC CCAAGGACCA CATGGTAACC    60

AGCTCCTTCT GCTGCCAGAG CNACGGCTGC AACANTGCCT TTNTGTCTGT NCCCTTGACC   120

AATCTNACTG AGAATNGCCT GATT                                         144
```

( 2 ) INFORMATION FOR SEQ ID NO:11:

( i ) SEQUENCE CHARACTERISTICS:
        ( A ) LENGTH: 174 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1LPB02
        ( B ) CLONE: 155045

( x i ) SEQUENCE DESCRIPTION: SEQ ID NO:11:

```
CNTGGCCTTA GTTTTNCNCT CACCCTCCNG GGTCTNGGGT GCCCACNACA CTGCGAANTA    60

TGTACGGCGG CGGGTAGCAG GTTCCATGNC CAAATNAAGA NCTTCANCNG TGACAAGGAC   120

ACATGTNTGC TCCTGGTCGG NAAGNCTACT TCAAAGGGCA AGGAGTTGGT GCAC         174
```

( 2 ) INFORMATION FOR SEQ ID NO:12:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1LPB02
        ( B ) CLONE: 156817

( x i ) SEQUENCE DESCRIPTION: SEQ ID NO:12:

```
CTGGCCTTTG TGTTGCTCTG CACCCTCCTG GGTCTTGGGT GCCCACTACA CTGCGAAATA    60

TGTACGGCGG CGGGGAGCAG GTGCCATGGC CAAATGAAGA CCTGCAGCAG TGACAAGGAC   120

ACATGTGTGC TCCTGGTCGG GAAGGCTACT TCAAAGGGCA AGGAGTTNGT GCACACCTAC   180

AAGGGCTGCA TCAT                                                    194
```

( 2 ) INFORMATION FOR SEQ ID NO:13:

( i ) SEQUENCE CHARACTERISTICS:
  ( A ) LENGTH: 224 base pairs
  ( B ) TYPE: nucleic acid
  ( C ) STRANDEDNESS: single
  ( D ) TOPOLOGY: linear ( i i ) MOLECULE TYPE: cDNA ( v i i ) IMMEDIATE SOURCE:
  ( A ) LIBRARY: PGANNOT01
  ( B ) CLONE: 619856

( x i ) SEQUENCE DESCRIPTION: SEQ ID NO:13:

```
AGAAAGAGAC  CATNCCAGGA  AGTTGTGGGG  TTGGGGAGGC  CTAGGGTTAG  GCAAGACCTT    60
GAGGCAGGGG  TTGAAGCCAG  GGAGTGGTCA  GCCAGCACTG  TCCCTGCCTG  TCCCCATCCC   120
ACAGAGGGCA  AGGAGTTGGT  GCACAACTAC  AAGGGCTGCA  TCAGGTCCCA  GGACTGCTAC   180
TNCGGNGTTA  TATCCACCAC  CATGGGCCCC  AAGGACCACA  TGGT                    224
```

( 2 ) INFORMATION FOR SEQ ID NO:14:

( i ) SEQUENCE CHARACTERISTICS:
    ( A ) LENGTH: 252 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: UTRSN0T02
    ( B ) CLONE: 683480

( x i ) SEQUENCE DESCRIPTION: SEQ ID NO:14:

```
GTTGGTGCAC  ACCTACAAGG  GCTGCATCAG  GTCCCAGGAC  TGCTACTCCG  GCGTTATATN    60
CACCACCATG  GGNCCCAAGG  ACCACATGGT  AACCAGCTCC  TTNTGCTGCC  AGAGCGACGN   120
CTGCAACAGT  GCCTTTTTGT  CTGTTCCCTT  GACCAATCTT  ACTGAGAATG  GCCTGATGTG   180
CCCCGNCTGC  ACTGCGAGCT  TNAGGGACAA  ATGCATGGGG  CCCATGACCC  ACTGTACTGG   240
AGAGGAAAAC  CA                                                          252
```

( 2 ) INFORMATION FOR SEQ ID NO:15:

( i ) SEQUENCE CHARACTERISTICS:
    ( A ) LENGTH: 250 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: BRAINOT11
    ( B ) CLONE: 1291208

( x i ) SEQUENCE DESCRIPTION: SEQ ID NO:15:

```
GGGAATCCCA  GTTCTTGCAG  CCACTGGGAA  TCAAGAGGCC  CAACTCCGTC  TTGGTCTTNN    60
NNNNNNNNN   NNNNNNNCAA  TGGGCCGGCC  GTGGGAAGGG  TGAATGTGGG  TCCAGACCCG   120
CCCCTCCTCA  GCTTCCTATA  AAAGCTGGGG  ACCAGGTACT  GCTGATACAC  ACACCATGAG   180
GCTCTCCAGG  AGACCAGAGA  CCTTTCTGCT  GGCCTTTGTG  TTGCTCTGCA  CCCTCCTGGG   240
TCTTGGGTGC                                                              250
```